(12) United States Patent
Johs et al.

(10) Patent No.: US 6,804,004 B1
(45) Date of Patent: Oct. 12, 2004

(54) MULTIPLE-ELEMENT LENS SYSTEMS AND METHODS FOR UNCORRELATED EVALUATION OF PARAMETERS IN PARAMETERIZED MATHEMATICAL MODEL EQUATIONS FOR LENS RETARDANCE, IN ELLIPOMETRY AND POLARIMETRY

(75) Inventors: Blaine D. Johs, Lincoln, NE (US); Craig M. Herzinger, Lincoln, NE (US); Ping He, Lincoln, NE (US); Martin M. Liphardt, Lincoln, NE (US)

(73) Assignee: J. A. Woollam Co., Inc, Lincoln, NE (US)

( * ) Notice: Subject to any disclaimer, the term of this patent is extended or adjusted under 35 U.S.C. 154(b) by 455 days.

(21) Appl. No.: 09/583,229

(22) Filed: May 30, 2000

Related U.S. Application Data

(63) Continuation-in-part of application No. 09/419,794, filed on Oct. 18, 1999, now Pat. No. 6,549,282, and a continuation-in-part of application No. 09/162,217, filed on Sep. 29, 1998, now Pat. No. 6,034,777, and a continuation-in-part of application No. 09/144,764, filed on Aug. 31, 1998, now Pat. No. 5,969,818, and a continuation-in-part of application No. 09/033,694, filed on Mar. 3, 1998, now Pat. No. 5,963,327.

(60) Provisional application No. 60/094,104, filed on Jul. 24, 1998.

(51) Int. Cl.[7] .............................................. G01B 11/06
(52) U.S. Cl. ....................................................... 356/369
(58) Field of Search ................................ 356/364, 369; 359/793, 795, 796

(56) References Cited

U.S. PATENT DOCUMENTS

| 415,040 A | * | 11/1889 | Hastings | 359/784 |
| 2,785,602 A | * | 3/1957 | Kohler | 359/748 |
| 2,865,253 A | * | 12/1958 | Thielens | 359/356 |

(List continued on next page.)

FOREIGN PATENT DOCUMENTS

| EP | 1 172 642 A2 | 11/2002 |
| JP | 229720 | 2/1994 |
| JP | 2002098591 A | 4/2002 |

OTHER PUBLICATIONS

"Automatic Rotating Element Ellipsometers: Calibration, Operation and Real-Time Applications", Collins, Rev. Sci. Instrum, 61(8) (1990), provides general insight.

(List continued on next page.)

Primary Examiner—Zandra V. Smith
(74) Attorney, Agent, or Firm—James D. Welch

(57) ABSTRACT

Disclosed are multi-element lenses which demonstrate reduced achromatic focal length and reduced electromagentic beam spot size dispersal effects in ellipsometer and polarimeter systems. Also disclosed is methodology for evaluating parameters in parameterized equations which enables calculating retardance entered to, or between, orthogonal components in a beam of electromagnetic radiation which is caused to pass through input and/or output optical elements and interact with a material system, by each of the input and output optical elements, substantially uncorrelated with retardation entered by the material system. Present invention input and/or output focusing lens(es) find application in spectroscopic ellipsometer mediated investigation of small spots on material systems, wherein a beam of electromagnetic radiation is caused to converge via an input lens, interact with a very small, chromatically undispersed spot area on a material system, then optionally re-collimate via an output lens, prior to entering a detector system. Present invention methodology provides benefit where it is necessary to separate out birefringent effects of input and/or output optical element focusing lens(es), optionally in combination with beam directing and/or window elements present in an ellipsometer system which are positioned with respect to input and/or output len(es) so as to be ellipsometrically indistinguishable therefrom, to arrive at material system characterizing ellipsometric PSI and DELTA results.

30 Claims, 7 Drawing Sheets

U.S. PATENT DOCUMENTS

| | | | | |
|---|---|---|---|---|
| 3,622,218 A | * | 11/1971 | Kruger | 359/356 |
| 4,516,855 A | | 5/1985 | Korth | 356/367 |
| 4,636,075 A | | 1/1987 | Knollenberg | 356/336 |
| 4,668,860 A | | 5/1987 | Anthon | 252/225 |
| 4,671,657 A | | 6/1987 | Calvani et al. | 356/349 |
| 4,854,686 A | * | 8/1989 | Oda | 359/795 |
| 4,893,932 A | | 1/1990 | Knollenberg | 356/369 |
| 5,166,752 A | | 11/1992 | Spanier et al. | 356/369 |
| 5,202,792 A | * | 4/1993 | Rollin | 359/356 |
| 5,333,052 A | | 7/1994 | Finarov | 356/364 |
| 5,349,471 A | | 9/1994 | Morris et al. | 359/565 |
| 5,373,359 A | | 12/1994 | Woollam et al. | 356/328 |
| 5,504,582 A | | 4/1996 | Johs et al. | 356/369 |
| 5,521,706 A | | 5/1996 | Green et al. | 356/369 |
| 5,582,646 A | | 12/1996 | Woollam et al. | 118/708 |
| 5,608,526 A | | 3/1997 | Piwonka-Corle et al. | 356/309 |
| 5,666,201 A | | 9/1997 | Johs et al. | 356/369 |
| 5,706,212 A | | 1/1998 | Thompson et al. | 364/525 |
| 5,757,494 A | | 5/1998 | Green et al. | 356/369 |
| 5,793,480 A | | 8/1998 | Lacey et al. | 356/73 |
| 5,798,837 A | | 8/1998 | Aspnes et al. | 356/369 |
| 5,877,859 A | | 3/1999 | Aspnes et al. | 356/364 |
| 5,917,594 A | * | 6/1999 | Norton | 356/327 |
| 5,963,327 A | | 10/1999 | He et al. | 356/369 |
| 5,978,087 A | | 11/1999 | Patterson et al. | 356/369 |
| 6,034,777 A | | 3/2000 | Johs et al. | 356/369 |
| 2002/0024669 A1 | | 2/2002 | Danner et al. | |

OTHER PUBLICATIONS

"Regression Calibration Method for Rotating Element Ellipsometers" Thin Solid Films, Johs, 234 (1993) is disclosed as it describes a mathematical regression based approach to calibrating ellipsometer systems.

"Systematic and Ramdom Errors in Rotating–Analyzer Ellipsometry", Nijs & Silfhout, J. Opt. Soc. Am. A., vol. 5, No. 6, (Jun. 1988), describes a first order mathematical correction factor approach to accounting for window effects in Rotating Analyzer ellipsometers.

"Systematic Errors in Rotating–Compensator ellipsometry", Kleim et al., J. Opt. Soc. Am., vol. 11, No. 9, (Sep. 1994) describes first order corrections for imperfections in windows and compensators in Rotating Compensator ellipsometers.

"Instrumental and Computational Advances for Real–time Processes Control Using Spectroscopic Ellipsometry", Pickering et al,Int. Conf. on Netrology and Charcterization for VSLI Tech., NIST, (Mar. 1998).

"Unified Analysis of Ellipsometry Errors Due to Imperfect Components Cell–Window Birifringence, and Incorrect Azimuth Angles", Azzam & Bashara; J. of the Opt. Soc. Am., vol. 61, No. 5, (May 1971).

"Analysis of Systematic Errors in Rotating–Analyzer Ellipsometers", Azzam & Bashara; J. of the Opt. Coc. Am., vol. 64, No. 11, (Nov. 1974).

"The Influence of Cell Window Imperfections on the Calibration and Measured Data of Two Types of Rotating Analyzer Ellipsometers", Azzam & Bashara; J. of the Opt. Soc. Am., vol. 61, No. 6, (Nov. 1971).

"The Influence of Cell Window Imperfections on the Calibration and Measured Data of Two Types of Rotating Analyzer Ellipsometers", Straaher et al., Surface Sci., North Holland, 96, (1980).

"In Situ Multi–Wavelength Ellipsometric Control of Thickness and Composition of Bragg Reflector Structures", by Herzinger, Johs, Reich, Caroenter & Van Hove, Mat. Res. Soc. Symp. Proc., vol. 406, (1996).

"A New Calculus For The Treatment Of Optical Systems", Jones, J.O.S. A., vol. 31, (Jul. 1941).

WO 91/14157 Published PCT Application.

WO 92/12404 Published PCT Application.

WO 96/18205 Published PCT Application.

WO 99/02950 Published PCT Application.

Copy of Dec. 1996 Vintage J.A. Woollam Co. M–44/M–88 Multiwavelength Ellipsometers indicating Focused Spot to 20 Microns, including signed Letter from Roger Bruhn, the photographer who took the pictures therein, which letter attests to the date it was produced.

Copy of SOPRA Brochure disclosing their MOSS System, which utilized Achromatic Focusing lenses and which predates Jul. 11, 2000. Sopra is a competitor of the J.A. Woollam Co. Inc.

Article from Oct. 1997 J. of Tribology titled "Flying Height Measurement on $Al_2O_3$ Film of a Magentic Slider" by Yufeng Li of Samsung; discloses use of a J.A. Woollam Co. M–44 Multiwavelength Ellipsometer to focus a beam to 17 microns. This system had doublet achromatic lenses installed therein.

Article from Thin Solid Films Published Mar. 27, 2000, by Zapien et al, showing use of achromatic focusing lenses before and after a sample in a spectroscopie ellipsomter.

Excerpts from a "classic" textbook titled OPTICS, by Hecht, Addison Wesley Press, (1977), which discribes use of Multiple Element Achromatic Lenses.

Articles from Thin Solid Films Published Apr. 1993, by El–Ghazzawi et al, showing use of focusing lenses in the SOPRA company model "MOSS ES–4G Spectroscopic Ellipsometer".

Two J.A. Woollam Co. spectroscopic ellipsometer "models" with achromatic multiple–element lenses sold prior to Jul. 11, 2000: M–44 (44 wavelengths, blue to red), and "VASE" (continuous wavelengths from blue to infrared).

Catalog pages of Edmund Scientific Corporation achromatic lens sets (dated prior to Jul 11, 2000).

J.A. Woollam Co., Inc. Purchase Orders from Edmund Scientific Company, with catalog cover dates and part numbers predating Jul. 11, 2000.

Evidence of sales (Purchase orders, shipping documents, invoices, from customers) of the "M–44" type spectroscopic ellipsometers containing achromatic focusing lenses prior to Jul. 11, 2000.

Order bills for M–44 Ellipsometer with achromatic focusing lenses for NANOmetrics Corporation. Order numbers correspond with "Packing List" and "Purchase Order Receiver" numbers listed in Erik Bylin's Affidavit.

Affidavit from John Woollam, President of J.A. Woollam Co.

Affidavit from Hiroki Hashimoto of Fujitsu Corporation, Japan in both English and Japanese; along with the Fujitsu purchase order sheet and Acceptance Report.

Affidavitt from Michio Suzuki of J.A. Woollam Co., Japan in both English and Japanese; along with purchase order sheet.

Affidavit from Geng Wang of Samsung Information Systems America, Inc.; along with the purchase order and original quotation.

Affidavit from Erik Bylin, Product Manager, NANOmetrics Corporation.

* cited by examiner

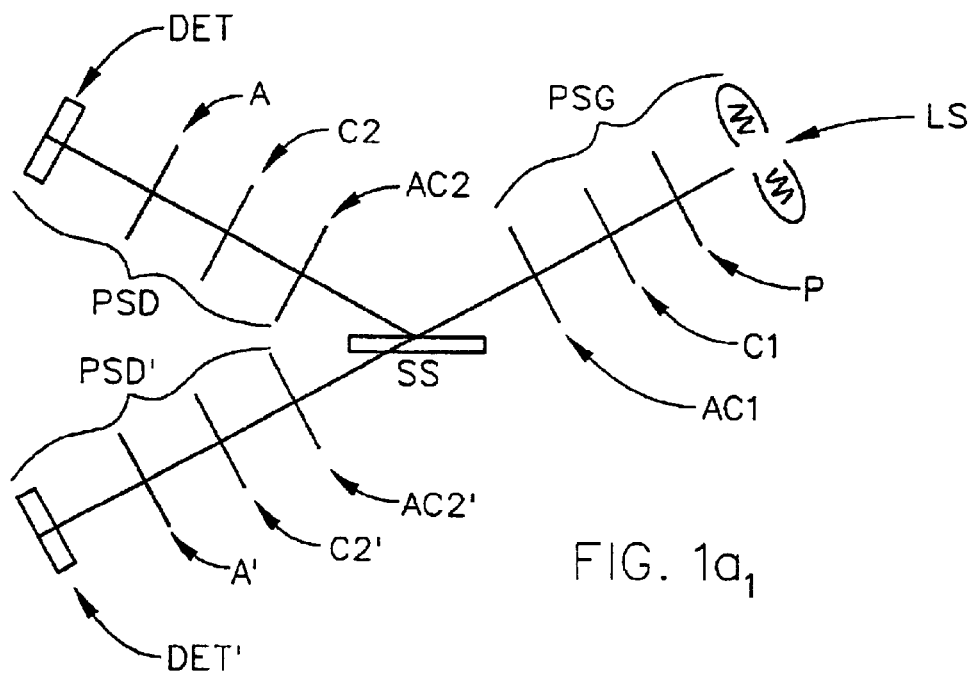
FIG. 1a₁
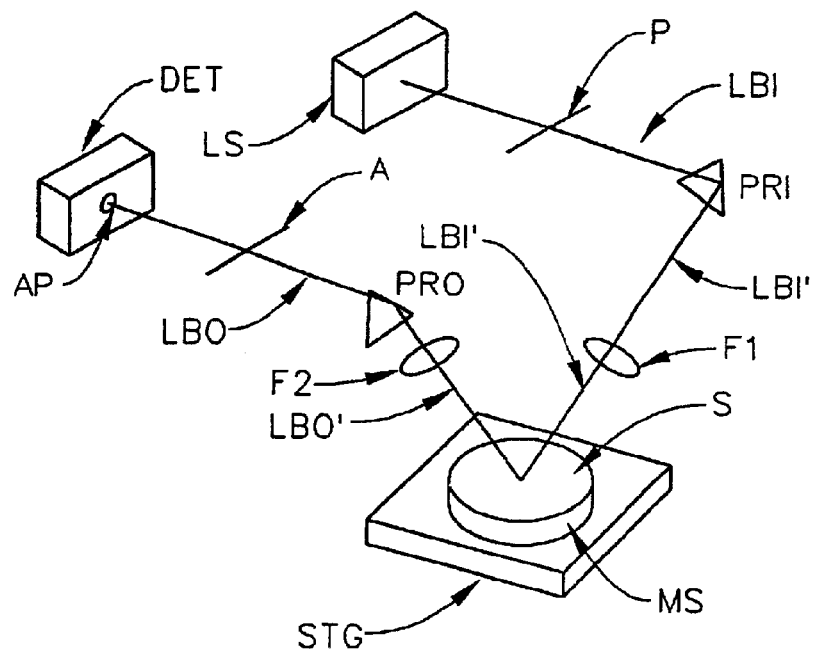
FIG. 1a₂

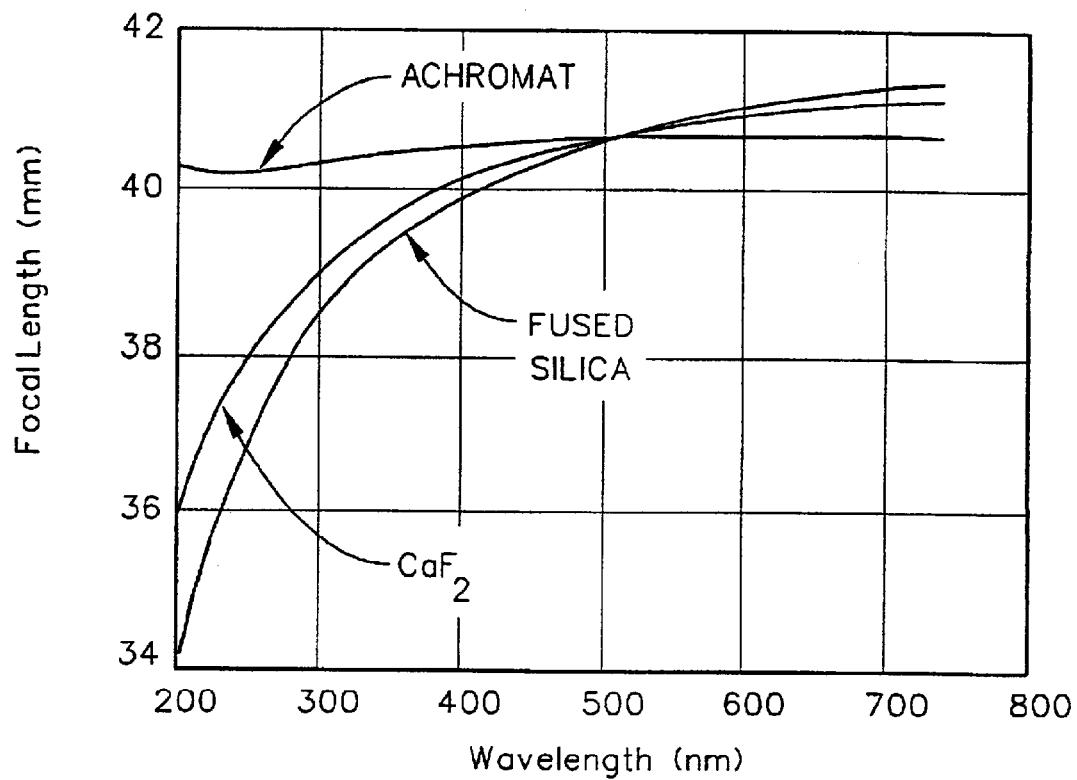
FIG. $1a_6$
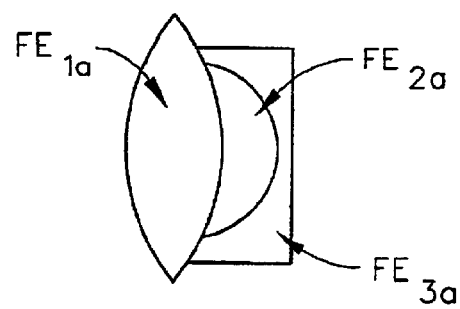
FIG. $1a_3$

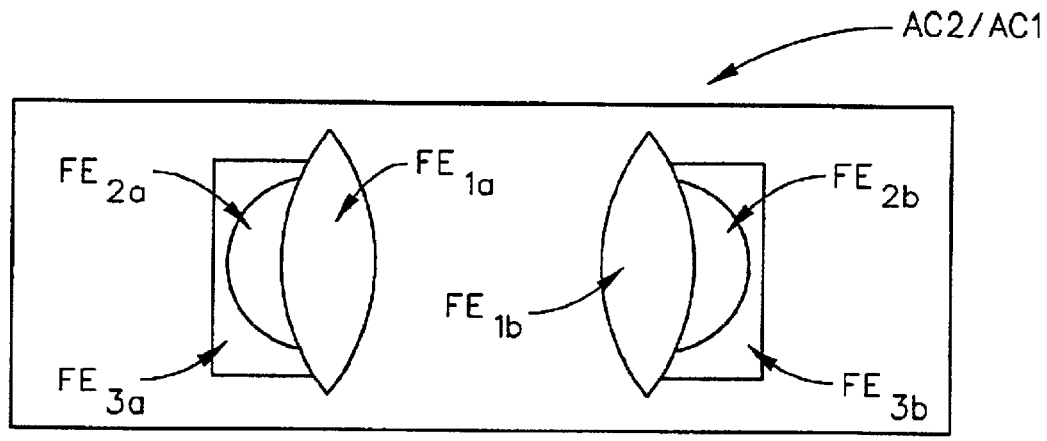
FIG. $1a_4$
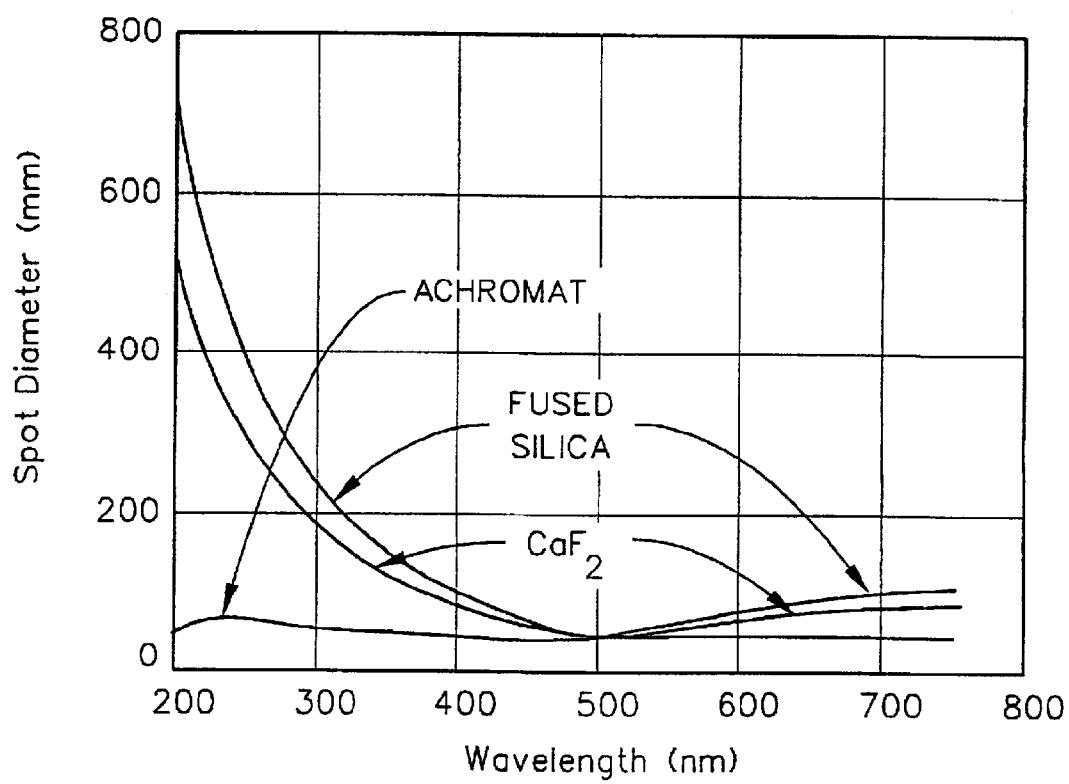
FIG. $1a_5$

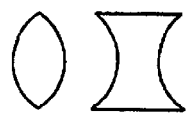
FIG. 1a₇
FIG. 1a₈
FIG. 1a₉
FIG. 1a₁₀
FIG. 1a₁₁
FIG. 1a₁₂
FIG. 1a₁₃
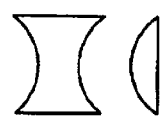
FIG. 1a₁₄
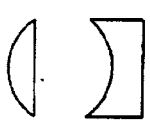
FIG. 1a₁₅
FIG. 1a₁₆
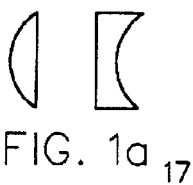
FIG. 1a₁₇
FIG. 1a₁₈
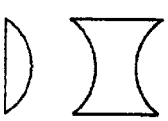
FIG. 1a₁₉
FIG. 1a₂₀
FIG. 1a₂₁
FIG. 1a₂₂
FIG. 1a₂₃
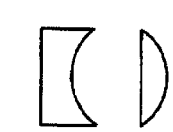
FIG. 1a₂₄
```
C  D  C  D           C  D  D  C
 FIG. 1a₂₅            FIG. 1a₂₆
D  C  D  C           D  C  C  D
 FIG. 1a₂₇            FIG. 1a₂₈
```

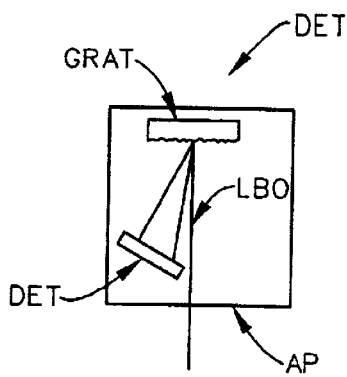
FIG. 1c
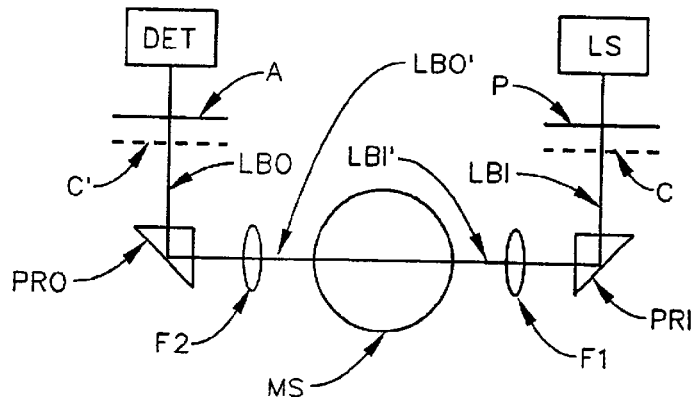
FIG. 2
FIG. 1b₁
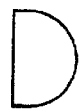
FIG. 1b₃
FIG. 1b₂
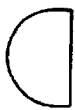
FIG. 1b₄

MULTIPLE-ELEMENT LENS SYSTEMS AND METHODS FOR UNCORRELATED EVALUATION OF PARAMETERS IN PARAMETERIZED MATHEMATICAL MODEL EQUATIONS FOR LENS RETARDANCE, IN ELLIPOMETRY AND POLARIMETRY

This Application a Continuation-in-part Of Allowed application Ser. No. 09/162,217, now U.S. Pat. No. 6,034,777, filed Aug. 29, 1998, and Allowed application Ser. No. 09/033,694, Now U.S. Pat. No. 5,963,327. filed Mar. 3, 1998, and Allowed application Ser. No. 09/144,764, now U.S. Pat. No. 5,969,818, filed Aug. 31, 1998, which depends from the 694 Application, and of Co-pending Ser. No. 09/419,794, now U.S. Pat. No. 6,549.282, filed Oct. 18, 1999, which application claims priority from Provisional Application 60/094104.

TECHNICAL FIELD

The present invention relates to ellipsometry and polarimetry, and more particularly comprises quasi-achromatic multi-element lens(es) and the application thereof in focusing, and optionally re-colliminating), a spectroscopic electromagnetic beam into a very small, chromatically relatively undispersed, area spot on a material system, said achromatic multi-element lens(es) providing relatively constant focal length at each wavelength in a large range of wavelengths, including into the deep UV; and said present invention is further a method for breaking correlation between, and evaluating parameters in parameterized equations for calculating retardance entered to, or between, orthogonal components in a beam of spectroscopic electromagnetic radiation by quasi-achromatic multi-element input and/or output optical elements, (eg. lens(es)), and a typically ellipsometrically indistinguishable, adjacently located, investigated material system with which the spectroscopic beam of electromagnetic radiation is caused to interact.

BACKGROUND

The practice of ellipsometry is well established as a non-destructive approach to determining characteristics of material systems, and can be applied in real time process control. The topic is generally well described in a number of publication, one such publication being a review paper by Collins, titled "Automatic Rotating Element Ellipsometers: Calibration, Operation and Real-Time Applications", Rev. Sci. Instrum, 61(8) (1990).

In general, modern practice of ellipsometry typically involves causing a spectroscopic beam of electromagnetic radiation, in an imposed, known, state of polarization, to interact with a material system at one or more angle(s) of incidence with respect to a normal to a surface thereof, in a plane of incidence. (Note, a plane of incidence contains both a normal to a surface of an investigated material system and the locus of said beam of electromagnetic radiation). Changes in the polarization state of said beam of electromagnetic radiation which occur as a result of said interaction with said material system are indicative of the structure and composition of said material system. The practice of ellipsometry utilizes said changes in polarization state by proposing a mathematical model of the ellipsometer system and the material system investigated by use thereof, obtaining experimental data by application of the ellipsometer system, and applying square error reducing mathematical regression, (typically), to the end that parameters in the mathematical model which characterize the material system are evaluated so that the obtained experimental data, and values calculated by use of the mathematical model have a "best match" relationship.

A typical goal in ellipsometry is to obtain, for each wavelength in, and angle of incidence of said beam of electromagnetic radiation caused to interact with a material system, material system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said material system;

$PSI = |r_p/r_s|$; and $DELTA = (\angle r_p - \angle r_s)$.

As alluded to, the practice of ellipsometry requires that a mathematical model be derived and provided for a material system and for the ellipsometer system being applied. In that light it must be appreciated that an ellipsometer system which is applied to investigate a material system is, generally, sequentially comprised of:

a. a Source of a beam electromagnetic radiation;
b. a Polarizer element;
c. optionally a compensator element;
d. (additional element(s) such as lens(es), beam directing means, and/or windows such as in vacuum chambers);
e. a material system;
f. (additional element(s) such as lens(es), beam directing means, and/or windows such as in vacuum chambers);
g. optionally a compensator element;
h. an Analyzer element; and
i. a Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems.

Where an ellipsometer system is applied to investigate a small region of a material system present, it must be appreciated that the beam of electromagnetic radiation can be convergently entered thereto through an input lens, and, optionally, exit via a re-collimating output lens. In effect this adds said input, go (and output), lenses as elements in the ellipsometer system as "additional elements", (eg. identified in d. and f. above), which additional elements must be accounted for in the mathematical model. If this is not done, material system representing parameters determined by application of the ellipsometer system and mathematical regression, will have the effects of said input, (and output), lenses at least partially correlated thereinto, much as if the input and, (output lenses), were integrally a part of the material system.

It is emphasized that where two sequentially adjacent elements in an ellipsometer system are held in a static positon with respect to one another while experimental ellipsometric data is acquired, said two sequentially adjacent elements generally appear to be a single element. Hence, a beam directing element adjacent to a lens can appear indistinguishable from said lens as regards the overall effect of said combination of elements. In that light it is to be understood that present input and output lenses are normally structurally fixedly positioned and are not rotatable with respect to a material system present in use, thus preventing breaking correlation between parameters in equations for sequentially adjacent input and output lenses and an investigated material system by an element rotation technique. While correlation of parameters in mathematical equations which describe the effects of groupings of elements, (such as a compensator and an optional element(s)), can be tolerable, correlation between parameters in the mathematical model of an investigated material system and other elements in the ellipsometer system must be broken to allow obtaining accurate material system representing PSI and DELTA values, emphasis added. That is to say that correlation between parameters in equations in a mathematical model which describe the effects of a stationary compensator and a sequentially next located lens element, (eg. correllation between effects of elements c. and d. or between f. and g. identified above), in a beam of electromagnetic radiation might be tolerated to the extent that said correlation does not influence determination of material system describing PSI and DELTA values, but the correlation between parameters in equations which describe the effects of ellipsometer system components (eg. a., b., c., d., f., g., h. and i.), and equations which describe the effects of a present material system (eq. element e. above), absolutely must be broken to allow the ellipsometer system to provide accurate PSI and DELTA values for said material system. Application of ellipsometry to investigation of a material system present can then present a challenge to users of ellipsometer systems in the form of providing a mathematical model for each of an input and output lens, and providing a method by which the effects of said input and output lenses can be separated from the effects of an investigated material system.

Thus is identified an example of a specific problem, solution of which is the topic of the present invention.

One typical approach to overcoming the identified problem, where space considerations are not critical, and where ellipsometer system configuration can be easily modified, is to obtain multiple data sets with an ellipsometer system configured differently during at least two different data set acquisitions. For instance, a data set can be obtained with a material system present and in which a beam of electromagnetic radiation is caused to interact with said material system, and another data set can be obtained with the ellipsometer system configured in a straight-through configuration, where a beam of electromagnetic radiation is caused to pass straight through an ellipsometer system without interacting with a material system. Simultaneous mathematical regression utilizing multiple data sets can allow evaluation of material system characterizing PSI and DELTA values over a range of wavelengths, uncorrelated with present birefringent retardation effects of present input and output lenses. The problem with this approach is that where ellipsometer systems are fit to vacuum chambers for instance, ellipsometer reconfiguration so as to allow acquisition of such multiple data sets can be extremely difficult, if not impossible to carry out.

Another rather obvious solution to the identified problem is to provide input, and output, lenses which are absolutely birefringence-free, and transparent at all electromagnetic beam wavelengths utilized. That is, provide input, and output, lenses which do not attenuate the magnitude of $r_p$ or $r_s$ orthogonal components, (or at least do not change their ratio, $r_p/r_s$), and which also do not enter phase shift between $r_p$ or $r_s$ orthogonal components when said beam of electromagnetic radiation is caused to pass therethrough. While control of the the effect of a lens on a ratio, ($r_{p/rs}$), of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc.

As described in Parent application Ser. No. 09/162,217, (which is incorporated herein by reference), controlling stress related change is presently achieved with varying degrees of success, where for instance, windows in a vacuum chamber are subject. Windows provided by BOMCO Inc. are produced with the goal of eliminating birefringence, and are mounted in vacuum chambers using copper gasket seals which help to minimize uneven application of stresses and developed strains thereacross. While some success is achieved via this approach, the BOMCO windows are not "perfect" and do demonstrate some remaining birefringence properties, which can vary in unpredictable ways over a period of usage. In addition, BOMCO windows are expensive,(costing on the order of $1000.00 each), and are large in size thereby making adaptation thereof to use in a vacuum chamber difficult at times, particularly in retro-fit scenarios. And, there have been cases where BOMCO windows have broken in use. This is highly undesirable as vacuum chambers are often times caused to contain highly toxic and hazardous materials during, for instance, etching and/or deposition steps required in the fabrication of semiconductor devices. Where vacuum chamber windows are the subject, an alternative to use of the BOMCO windows is to simply use standard vacuum chamber windows, which, while significantly less expensive, demonstrate order of magnitude larger birefringence effects. (Note, BOMCO windows provide birefringent effects on the order of approximately six-tenths (0.6) to two-tenths (0.2) degrees over a range of wavelengths of from four-hundred (400) to seven-hundred-fifty (750) nanometers, whereas standard vacuum windows demonstrate birefringent effects on the order of six (6.0) to three (3.0) degrees over the same range of wavelengths). (Note, birefringent retardation typically follows an approximate inverse wavelength, (eg. 1/wavelength), relationship). However, where standard vacuum chamber windows are utilized, compensation of their effects is required. Similar concerns apply where input and output lenses, and associated ellipsometrically indistinguishable ellipsometer system components are concerned.

A need is thus identified for a method of practicing ellipsometry which enables the breaking of correlation between parameters in equations which describe retardance entered to orthogonal components of a beam of electromagnetic radiation caused to interact with a material system, and parameters in equations which describe birefringent effects on said orthogonal components in said beam of electromagnetic radiation caused by input and output windows of a vacuum chamber, and/or by input and output lenses and/or by electromagnetic beam directing means etc.

Various researchers have previously noted the identified problem, where vacuum chamber windows are the topic, and proposed various first order mathematical model equation correction techniques as solution, which approaches have met with various degrees of success where vacuum chamber input and output windows demonstrate on the order of a maximum of two (2) degrees of birefringence. This, however, leaves the problem unsolved where birefringence approaches six (6.0) degrees, as commonly occures in standard vacuum chamber windows, and can also occur in lens systems, particlarly at wavelengths of four-hundred (400) nanometers and below. Thus is identified a problem to which the present invention calibration methodology applies.

Patents of which the Inventor is aware include U.S. Pat. No. 5,757,494 to Green et al., in which is taught a method for extending the range of Rotating Analyzer/Polarizer ellipsometer systems to allow measurement of DELTAS near zero (0.0) and one-hundred-eighty (180) degrees. Said Patent describes the presence of a window-like variable birefringent components which is added to a Rotating Analyzer/Polarizer ellipsometer system, and the application thereof during data acquisition, to enable the identified capability.

A Patent to Thompson et al. U.S. Pat. No. 5,706,212 teaches a mathematical regression based double fourier series ellipsometer calibration procedure for application, primarily, in calibrating ellipsometers system utilized in infrared wavelength range. Birefringent window-like compensators are described as present in the system thereof, and discussion of correlation of retardations entered by sequentially adjacent elements which do not rotate with respect to one another during data acquisition is described therein.

A Patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertian to Rotating Analyzer ellipsometer systems.

Patents identified in a Search specifically focused on the use of lenses, preferrably achromatic, in ellipsometry and related systems are:

U.S. Pat. Nos. 5,877,859 and 5,798,837 to Aspnes et al.;

U.S. Pat. No. 5,333,052 to Finarov;

U.S. Pat. No. 5,608,526 to Piwonka-Corle et al.;

U.S. Pat. No. 5,793,480 to Lacy et al.;

U.S. Pat. Nos. 4,636,075 and 4,893,932 to Knollenberg; and

U.S. Pat. No. 4,668,860 to Anthon.

The most relevant Patent found is U.S. Pat. No. 5,917,594 to Norton. However, the system disclosed therein utilizes a spherical mirror to focus an electromagentic beam onto the surface of a sample in the form of a small spot. Said system further develops both reflection and transmission signals via application of reflective means and of reflection and transmission detectors. The somewhat relevant aspect of the 594 Patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferrably zero. It is noted that, as described elsewhere in this Specification, said 594 Patent lens structure, positioning in the 594 Patent system, and purpose thereof are quite distinct from the present invention lens structure and application to focus a beam of electromagnetic radiation. In particular, note that the 594 Patent lens is not applied to directly focus and/or recollimate a beam of electromagnetic radiation onto a sample system, as do the lenses in the present invention. And, while the present invention could utilize a meniscus lens in an embodiment thereof, the 594 Patent specifically requires and employs a negative meniscus lens to correct for spherical aberabtions caused by off-axis reflection from a spherical mirror, in combination with a positive lens to correct for achromatic aberation introduced by said negative meniscus lens. Further, the present invention system does not require reflection means be present in the path of an electromagnetic beam after its passage through the focusing lens thereof and prior to interacting with a sample system, as does the system in the 594 Patent wherein a focusing spherical mirror is functionally required.

Various papers were also identified as possibly pertinant, and are:

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Nijs & Silfhout, titled "Systematic and Random Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (setp. 1994) describes first order corrections for imperfections in windows and compensators in Rotating Compensator ellipsometers.

Other papers of interest in the area by Azzam & Bashara include one titled "Unified Analysis of Ellipsometry Erors Due to Imperfect Components Cell-Window Birifringence, and Incorrect Azimuth Angles", J. of the Opt. Soc. Am., Vol 61, No. 5, (May 1971) and one titled "Analysis of Systematic Errors in Rotating-Analyzer Ellipsometers", J. of the Opt. Soc. Am., Vol. 64, No. 11, (Nov. 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment of Optical Systems", J.O.S.A., Voil. 31, (July 1941), is also identified as it describes the characterizing of multiple lens elements which separately demonstrate birefringence, as a single lens, (which can demonstrate reduced birefringence).

Finally, a paper which is co-authored by inventors herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of relevant prior art, there remains need for ellipsometer systems which comprise input, and optionally output, lenses that allow focusing spectroscopic electromagnetic beams as small spots on material substrates. Further, in view of the inability of first order corrections to break birefringence based correlation between input and/or output lenses and a material system, there remains need for a second order mathematical model equation correction technique which enables breaking correlation between a material system characterizing DELTA and in-plane retardance entered to a beam of electromagnetic radiation by input and output lenses through which said beam of electromagnetic radiation is caused to pass. This is particularly true where lens birefringent retardance exceeds a few degrees. The present invention responds to said identified needs.

DISCLOSURE OF THE INVENTION

The present invention system basically comprises a lens system, primarily as applied in ellipsometer and polarimeter systems wherein birefringence, and spectroscopic electromagnetic beam spot size chromatic dispersion reduction and focal length chromatic dispersion reduction is desired, but wherein spherical, coma distortion, third order aberations, astigmatism and image reproduction are substantially unimportant considerations. A single stage present invention lens system has a focal length of one-hundred millimeters or less, (nominally about eighty millimeters), and said lens system comprises two sequentially oriented elements, one of said two sequentially oriented elements being of a shape and orientation which individually converges a beam of electromagnetic radiation caused to pass therethrough, and the other being of a shape and orientation which individually diverges, (to a lesser degree than said convergence), a beam of electromagnetic radiation caused to pass therethrough, there being a region between said first and second elements. A present invention dual stage lens system provides a less than fifty millimeter, (nominal about forty millimeter), focal length and is comprised of four sequentially oriented lens elements which are grouped into two groups of two elements each, two of which four elements are converging and two of which are diverging of electromagenic radiation caused to pass therethrough.

It is to be understood that, in use, a beam of electromagnetic radiation sequentially passes through one of said first and second elements in a single present invention lens system, then said region therebetween, and then through said second of said first and second elements before emerging as a focused beam of electromagnetic radiation, said region between said first and second elements have essentially the optical properties of a void region, or functional equivalent. In a dual stage present invention lens system a second stage of first and second elements is present in the electromagnetic beam pathway.

Further, present invention lens systems are characterized as quasi-achromatic as a result of multi-element construction, wherein, for each said two element lens systems present, the two elements thereof are made from different materials, (eg. one from what is commonly termed Crown-glass and one from Flint-glass in the literature). Again, as a result of present invention lens construction, very small electromagnetic beam spot focusing on an investigated material system is possible over a large range of wavelengths, (including transmitting properties into the deep UV), because of reduced chromatic focal length and spot size dispersion. It is noted that said present invention multi-element ellipsometer system input (and output) lenses can both (when present) demonstrate birefringence; neither demonstrate birefringence or one can demonstrate birefringence and the other not demonstrate birefringence. In fact, one non-birefringent input or output lens can be absent but for a consideration of its presence as essentially surrounding atmospheric ambient, or equivalent thereto.

A present invention lens system, which is particulary well suited for application in ellipsometer systems, provides for spectroscopic electromagnetic beam spot size and focal length chromatic dispersion reduction by configuring at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation. Such a lens system with application in ellipsometer systems is characterized by a converging element which presents as a selection from the group consisting of:

a bi-convex;

a plano-convex with an essentially flat side;

and said diverging element is characterized as a selection from the group consisting of:

a bi-concave lens element;

a plano-concave with an essentially flat side.

Further, as shown in FIGS. 1$a$7–1$a$24, said present invention lens systems can comprise a selection from the group consisting of:

a) a sequential combination of a bi-convex element and a bi-concave element;

b) a sequential combination of a bi-concave element and a bi-convex element;

c) a sequential combination of a bi-convex element and a plano-concave element with said concave side of said plano-concave element adjacent to said bi-convex element;

d) a sequential combination of a bi-convex element and a plano-concave element with said essentially flat side of said plano-concave element being adjacent to said bi-convex element;

e) a sequential combination of a plano-concave element and a bi-convex element with said essentially flat side of said plano-concave element adjacent to said bi-concave element;

f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;

h) a sequential combination of a bi-concave element with a plano-convex element with said convex side of said plano-convex element adjacent to said bi-concave element;

i) a sequential combination of a piano-concave element and a plano-convex element with the essentially flat side of said plano-concave element being adjacent to the convex side of the plano-convex element;

j) a sequential combination of a plano-concve element and a plano-convex element with the essentially flat side of said plano-concave element being adjacent to the convex side of said plano-convex element;

k) a sequential combination of a plano-convex element and a plano-concave element with the essentially flat side of said plano-covex element and the essentially flat side of said plano-concave element being adjacent to one another;

l) a sequential combination of a plano-concave element and a plano-convex element with the concave side of said plano-concave element being adjacent to the convex side of the plano-convex element;

m) a sequential combination of a plano-convex element and a bi-concave element with said convex side of said plano-convex element adjacent to said bi-concave element;

n) a sequential combination of a bi-concave element and a plano-convex element with said essentially flat side of said plano-convex element adjacent to said bi-concave element;

o) a sequential combination of a plano-convex element and a plano-concave element with said convex side of said plano-convex element adjacent to the concave side of the plano-concave element;

p) a sequential combination of a plano-concave element and a plano-convex element with said essentially flat side of said plano-convex element being adjacent to the essentially flat side of the plano-concave element;

q) a sequential combination of a plano-convex element and a plano-concave element with said convex side of said plano-convex element being adjacent to the essentially flat side of the plano-concave element; and r) a sequential combination of a plano-concave element with a plano-convex element with the essentially flat side of said plano-convex element being adjacent to the concave side of said plano-concave element;

and wherein said region between said first and second elements having essentially the optical properties of a selection from the group consisting of:

a void region; and a functional equivalent to a void region.

A present invention lens system with application in ellipsometer systems can be further characterized in that the converging element of said first and second elements is typically made of a material independently selected from the group consisting of:

$CaF_2$;

$BaF_2$;

LiF; and $MgF_2$;

and the diverging element of said first and second elements is selected to be made of fused silica, although it is within the scope of the present invention to make the converging element of fused silica and the diverging element of a selection from the group consisting of $CaF_2$; $BaF_2$; LiF; and $MgF_2$. It is noted that lens elements made of $MgF_2$ are typically bi-refringent whereas lens elements made of $CaF_2$; $BaF_2$ and LiF typically demonstrate far less bi-refringence, unless subjected to stress.

A present invention lens system with a focal lenght of fifty millimeters or less, with application in ellipsometer systems, can be described as being comprised of lens system comprising two sequentially oriented lenses, each of said sequentially oriented lenses being comprised of:

at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation; said lens system being described by a selection, as shown in FIGS. 1a25–1a28, from the group consisting of:

1. a sequential combination of a converging element (C), a diverging element (D), a converging element (C) and a diverging element (D);

2. a sequential combination of a converging element (C), a diverging (D) element, a diverging (D), element and a converging (C) element;

3. a sequential combination of a diverging element (D), a converging element (C), a diverging (D) element and a converging (C) element;

4. a sequential combination of a diverging element (D), a converging element (C), a converging element (C) and a diverging (D) element.

And, of course, other sequential lens element configurations within the scope of the present invention include:

(Converging(C))(Converging(C)(Diverging();

(Diverging(D))(Diverging(D))(Converging(C);

(Converging(C))(Diverging(D))(Diverging(D));

(Diverging(D))(Converging(C))(Diverging(DD));

(Converging(C))(Converging(C)(Diverging(D))(Diverging(D)); and (Diverging(D)(Diverging(D))(Converging(C))(Converging(C)).

One embodiment of a present invention lens system is further characterized by at least one selection from the group consisting of:

a. the focal length of the lens system is between forty (40) and forty-one (41) millimeters over a range of wavelengths of at least two-hundred (200) to seven-hundred (700) nanometers; and b. the focal length of the dual stage lens system varies by less than five (5%) percent over a range of wavelengths of between two-hundred and five-hundred nanometers; and c. the spot diameter at the focal length of the lens system is less than seventy-five (75) microns over a range of wavelengths of at least two-hundred (200) to seven-hundred (700) nanometers.

(It is noted that the listing of single two element lens constructions (a) through (r) above provides insight to applicable converging and diverging lens element combinations in dual stage lens systems).

It is specifically noted that the present invention includes the case of an ellipsometer system in which only one of said multi-element input or output lenses is present, (typically only the input lens), and the case wherein both input and output lenses are present, but only one is of multiple element construction, and/or demonstrates bi-refringence.

A prefered present invention single two element lens system is constructed from a Bi-convex lens element made of $CaF_2$, (eg. JANOS Technology Inc. Part No. A1407-003), functionally combined with a Fused Silica Plano-Concave lens element, (eg. OptoSigma Inc. Part No. 012-0080), in a manner generally indicated by FIG. 1a3.

Continuing, it is further noted that various beam directing means, such as mirror systems, enable providing small, spectroscopically essentially undispersed, electromagnetic beam spot size at a material system, but that most such mirror systems are birefringent, in that they retard orthogonal components of a polarized electromagnetic beam reflecting therefrom, by different amounts.

Further, while present invention multi-element lenses in ellipsometric settings are typically relatively less birefringent and chromatically dispersive than are, for instance, electromagnetic beam directing mirror systems, in the case where a present invention multi-element input and/or output optical element(s) demonstrates birefringence, the present invention is further a method of accurately evaluating parameters in parameterized equations in a mathematical model of a system of spatially separated input and output elements, (herein beneficially, demonstratively, identified as lenses), as applied in an ellipsometry or polarimetry setting. Said parameterized equations enable, when parameters therein are properly evaluated, independent calculation of retardance entered by each of said multi-element input lens and said multi-element output lens to, or between, orthogonal components of a beam of electromagnetic radiation caused to pass through said input and output lenses. This provides utility in the form of enabling the breaking of correlation between retardance entered between orthogonal components in a spectroscopic electromagetic beam by input and output lenses and by a material system under investigation. (It is to be understood that at least one of said multi-element input and output lenses in a present invention ellipsometer is often at least somewhat birefringent even though it is quasi-achromatic regarding focal length over a relativley wide wavelength range).

In a basic sense, the present invention method of breaking correlation between retardance effects caused by present invention multi-element input and/or output lenses in an ellipsometer system, and retardance effects caused by an adjacent, otherwise ellipsometrically undistinguishable material system being investigated comprises, in any functional order, the steps of:

a. providing spatially separated input and output optical element (eg. lenses), at least one of said input output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system, the composition of said material system being sufficiently well known so that retardance entered thereby to a polarized beam of electromagnetic radiation of a given wavelength, which is caused to interact with said material system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said input and output lenses and said material system, comprising separate parameterized equations for independently calculating retardance entered between orthogonal components of a beam of electromagnetic radiation caused to pass through each of said input and output lenses and interact with said material system in a plane of incidence thereto; such that where parameters in said mathematical model are properly evaluated, retardance entered between orthogonal components of a beam of electromagnetic radiation which passes through each of said input and output lenses and interacts with said material system in a plane of incidence thereto can be independently calculated from said parameterized equations, given wavelength;

e. obtaining a spectroscopic set of ellipsometric data with said parameterizable material system present on the means for supporting a material system, utilizing a beam of electromagnetic radiation provided by said source of electromagnetic radiation, said beam of electromagnetic radiation being caused to pass through said input lens, interact with said parameterizable material system in a plane of incidence thereto, and exit through said output lens and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input lens, interact with said material system in a plane of incidence thereto, and exit through said output lens.

The end result of practice of said method is that application of said parameterized equations for each of said input lens, output lens and material system for which values of parameters therein have been determined in step f., enables independent calculation of retardance entered between orthogonal components of a beam of electromagnetic radiation by each of said input and output lenses, and said material system, at given wavelengths in said spectroscopic set of ellipsometric data. And, it is emphasized that said calculated retardance values for each of said input lens, output lens and material system are essentially uncorrelated.

It is further to be appreciated that one of said input or output lenses can be physically absent entirely, which is the equivalent to considering it to be simply surrounding ambient atmosphere with associated non-birefringent properties. The language "providing spatially separated input and output lenses, at least one of said input and output lenses demonstrating birefringence when a beam of electromagnetic radiation is caused to pass therethrough", is to be interpreted to include such a situation wherein a non-birefringent lens is simply atmospheric ambient or an optical equivalent. Additionally, it is to be understood that input optical elements can comprise beam directing means and window(s), (as in a vacuum chamber), in addition to input lens(es); and that optput optical elements can comprise selection beam directing means and window(s), (as in a vacuum chamber), as well as output lens(es).

As further discussed later herein, a modification to the just recited method can be to, (in the step d. provision of a mathematical model for said ellipsometer system and said input and output lenses and said parameterizable material system for each of said input and output lenses), provide separate parameterized mathematical model parameterized equations for retardance entered to each of said two orthogonal components of a beam of electromagnetic radiation caused to pass through said input and output lenses. When this is done, at least one of said orthogonal components for each of said input and output lenses is directed out of the plane of incidence of said electromagnetic beam onto said parameterizable material system. And, typically, though not necessarily, one orthogonal component will be aligned with the plane of incidence of said electromagnetic beam onto said parameterizable material system. When this is done, calculation of retardation entered between orthogonal components of said beam of electromagnetic radiation, given wavelength, by said input lens is provided by comparison of retardation entered to each of said orthogonal components for said input lens, and such that calculation of retardation entered between orthogonal components of said beam of electromagnetic radiation, given wavelength, by said output lens is provided by comparison of retardance entered to each of said orthogonal components for said output lens.

It is pointed out that the step f. simultaneous evaluation of parameters in said mathematical model parameterized equations for said parameterizable material system, and for said input and output lenses, is typically, though not necessarily, achieved by a square error reducing mathematical curve fitting procedure.

It is important to understand that in the method recited earlier, the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data typically involves obtaining data at a plurality of settings of at least one component selected from the group consisting of: (said analyzer and said polarizer). As well, it is to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

It is also to be understood that the step of providing separate parameterized mathematical model parameterized equations for enabling independent calculation of retardance entered by said input said output lenses between orthogonal components of a beam of electromagnetic radiation caused to pass through said input and output lenses preferably involves parameterized equations having a form selected from the group consisting of:

$$ret(\lambda) = (K1/\lambda)$$
$$ret(\lambda) = (K1/\lambda)*(1+(K2/\lambda^2))$$
$$ret(\lambda) = (K1/\lambda)*(1+(K2/\lambda^2)+(K3/\lambda^4))$$

A modified method of accurately evaluating parameters in parameterized equations in a mathematical model of a system of spatially separated input and output lenses, said parameterized equations enabling, when parameters therein are properly evaluated, independent calculation of retardation entered by each of said input lens and said output lens to at least one orthogonal component(s) of a beam of electromagnetic radiation caused to pass through said input and output lenses, at least one of said input and output lenses being birefringent, said method comprising, in a functional order, the steps of:

a. providing spatially separated input and output lenses, at least one of said input and output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system;

d. providing a mathematical model for said ellipsometer system and said input and output lenses and said material system, comprising, for each of said input lens and said output lens, separate parameterized equations for retardance for at least one orthogonal component in a beam of electromagnetic radiation provided by said source of electromagnetic radiation, which orthogonal component is directed out of a plane of incidence which said electromagnetic beam makes with said material system in use, and optionally providing separate parameterized equations for retardance for an in-plane orthogonal component of said beam of electromagnetic radiation, such that retardation entered to said out-of-plane orthogonal component, and optionally to said in-plane orthogonal component, of said beam of electromagnetic radiation by each of said input and output lenses, can, for each of said input and output lenses, be separately calculated by said parameterized equations, given wavelength, where parameters in said parameterized equations are properly evaluated;

e. obtaining a spectroscopic set of ellipsometric data with said material system present on the means for supporting a material system, utilizing a beam of electromagnetic radiation provided by said source of electromagnetic radiation, said beam of electromagnetic radiation being caused to pass through said input lens, interact with said material system in a plane of incidence thereto, and exit through said output lens and enter said detector system;

f. by utilizing said mathematical model provided in step d. and said spectroscopic set of ellipsometric data obtained in step e., simultaneously evaluating material system DELTA'S in correlation with in-plane orthogonal component retardation entered to said beam of electromagnetic radiation by each of said input and output lenses, and parameters in said mathematical model parameterized equations for out-of-plane retardance entered by said input lens and said output lens to a beam of electromagnetic radiation caused to pass through said input lens, interact with said material system in said plane of incidence thereto, and exit through said output lens.

Again, application of said parameterized equations for out-of-plane retardance entered by said input lens and said output lens to a beam of electromagnetic radiation caused to pass through said input lens, interact with said material system in said plane of incidence thereto, and exit through said output lens, for which values of parameters therein are determined in step f., enables independent calculation of retardance entered to said out-of-plane orthogonal component of a beam of electromagnetic radiation by each of said input and output lenses, given wavelength.

Also, again the step f. simultaneous evaluation of parameters in said mathematical model parameterized equations for calculation of retardance entered to said out-of-plane orthogonal component of a beam of electromagnetic radiation by each of said input and output lenses, given wavelength, and said correlated material system DELTA'S and retardance entered to said in-plane orthogonal component of a beam of electromagnetic radiation by each of said input and output lenses, is typically achieved by a square error reducing mathematical curve fitting procedure.

It remains, in the presently disclosed method, to provide values for parameters in the in-plane parameterized equations for retardation, in said mathematical model of a system of spatially separated input and output lenses. The presently disclosed method therefore further comprises the steps of:

g. providing a parameterized equation for retardation entered by said material system to the in-plane orthogonal component of a beam of electromagnetic radiation, and as necessary similar parameterized equations for retardation entered by each of said input and output lenses to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said material system and by said input lens and said output lens such that the correlation between material system DELTA'S and the retardance entered by said in-plane orthogonal component of a beam of electromagnetic radiation by each of said input and output lenses, at given wavelengths in said spectroscopic set of ellipsometric data, is broken.

The end result of practice of the immediately foregoing steps a.–h. is that application of said parameterized equations for each of said input lens, output lens and material system for which values of parameters therein have been determined in step h., enables independent calculation of retardance entered to both said out-of-plane and said in-plane orthogonal components of a beam of electromagnetic radiation by each of said input and output lenses, and retardance entered by said material system to said in-plane orthogonal component of said beam of electromagnetic radiation, at given wavelengths in said spectroscopic set of ellipsometric data.

As before for other parameter evaluation steps, the step h. simultaneous evaluation of parameters in said mathematical model parameterized equations for said in-plane retardation entered by said parameterized material system, and said input and output lenses, is typically achieved by a square error reducing mathematical curve fitting procedure.

If the material system present can not be easily parameterized, the presently disclosed method of accurately evaluating parameters in parameterized equations in a mathematical model of a system of spatially separated input and output lenses, provides that the following steps, g.–j. be practiced:

g. removing the material system from said means for supporting a material system positioned between said input and output lenses, and positioning in its place an alternative material system for which a parameterized equation for calculating in-plane retardance entered to a beam of electromagnetic radiation, given wavelength, can be provided;

h. providing a parameterized equation for retardation entered in-plane to an orthogonal component of a beam of electromagnetic radiation by said alternative material system which is then positioned on said means for supporting a material system positioned between said input and output lenses, and as necessary similar parameterized equations for retardation entered by each of said input and output lenses to the in-plane orthogonal component of a beam of electromagnetic radiation;

i. obtaining a spectroscopic set of ellipsometric data with said alternative material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system;

j. by utilizing said parameterized mathematical model for said input lens and said output lens provided in step d. and said parameterized equation for retardation entered by said alternative material system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative material system and by said input lens and said output lens, such that correlation between DELTA'S entered by said alternative material system and retardance entered by said in-plane orthogonal component of said beam of electromagnetic radiation, by each of said input and output lenses, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said input lens and said output lens;

The end result being that application of said parameterized equations for each of said input lens and output lens and alternative material system, for each of which values of parameters therein have been determined in step j., enables independent calculation of retardance entered to both said out-of-plane and said in-plane orthogonal components of a beam of electromagnetic radiation by each of said input lens and said output lens, and retardance entered by said alternative material system to said in-plane orthogonal component of a beam of electromagnetic radiation, at given wavelengths in said spectroscopic set of ellipsometric data.

As before, said presently disclosed method of accurately evaluating parameters in parameterized equations in a mathematical model of a system of spatially separated input and output lenses provides that in the step j. simultaneous evaluation of parameters in said mathematical model parameterized equations for said in-plane retardation entered by said parameterized material system, and at least said in-plane input lens and output lens, is typically achieved by a square error reducing mathematical curve fitting procedure.

As mentioned with respect to the first method of the present invention disclosed herein, the presently disclosed method of accurately evaluating parameters in parameterized equations in a mathematical model of a system of spatially separated input and output lenses provides that the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data involves obtaining data at a plurality of settings of at least one component selected from the group consisting of: (said analyzer and said polarizer). As well, it is again to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

Said presently disclosed method of accurately evaluating parameters in parameterized equations in a mathematical model of a system of spatially separated input and output lenses also provides that the step of providing separate parameterized mathematical model parameterized equations for enabling independent calculation of out-of-plane and in-plane retardance entered by said input said output lenses to said beam of electromagnetic radiation caused to pass through said input and output lenses involve parameterized equations having a form selected from the group consisting of:

$$ret(\lambda) = (K1/\lambda)$$
$$ret(\lambda) = (K1/\lambda)*(1+(K2/\lambda^2))$$
$$ret(\lambda) = (K1/\lambda)*(1+(K2/\lambda^2)+(K3/\lambda^4))$$

It is again noted that while the present invention can be practiced with any type "lenses", be there one or two of them, (ie. one, or both, of the input or output lenses can be essentially non-birefringent and even ambient), and while an input lens or output lens can be considered to be formed by a plurality of elements, (eg. two elements made of different materials such as Fused Silica and Calcium Fluoride), the step a. providing of spatially separated input and output lenses is best exemplified as being practiced by the providing of an ellipsometer system that has both input and output lenses present therein through which an beam of electromagnetic radiation is caused to convergently enter and exit in a recolliminated form, repectively.

Any method of the present invention can further involve, in a functional order the following steps a1.–a4:

a1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and a2. causing an unknown material system to be present on said means for supporting a material system;

a3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and a4. by utilizing said mathematical model for said input lens and said output lens in which parameter values in mathematical model parameterized equations, for each of said input lens and output lens have been fixed, simultaneously evaluating PSI'S and uncorrelated DELTA'S parameters for said unknown material system.

As in other steps in the present invention method in which parameter values are evaluated, it is again noted that the method of accurately evaluating parameters in parameterized equations in a mathematical model of a system of spatially separated input and output lenses in which said simultaneous evaluation of PSI'S and DELTA'S for said unknown material are typically achieved by a square error reducing mathematical curve fitting procedure.

As alluded to earlier, the step of providing spatially separated input and output lenses, at least one of said input and output lenses demonstrating birefringence when a beam of electromagnetic radiation is caused to pass therethrough, can involve one or both lens(es) which is/are not birefringent. And, said at least one lens which is not birefringent can be essentially a surrounding ambient, (ie. a phantom lens which is essentially just the atmosphere surrounding a material system).

It is noted that where parameters in parameterized equations for out-of-plane retardance equations have been determined, a focused version of the present invention method for accurately evaluating parameters in parameterized equations in a mathematical model of a system of spatially separated input and output lenses can comprise the steps of b1–b7:

b1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and b2. causing an unknown material system to be present on said means for supporting a material system;

b3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and b4. by utilizing said mathematical model for said input lens and said output lens in which parameter values in mathematical model parameterized equations, for each of said input lens and output lens have been fixed, simultaneously evaluating ALPHA'S and BETA'S for said unknown material system, (see the Detailed Description for definition of ALPHA'S and BETA'S);

b5. applying transfer functions to said simultaneously evaluated ALPHA'S and BETA'S for said unknown material system to the end that a data set of effective PSI's and DELTA's for a combination of said lenses and said material system is provided;

b6. providing a mathematical model for said combination of said lenses and said material system which separately accounts for the retardation effects of the presence of said lenses and said material system by parameterized equations; and b7. by utilizing said mathematical model for said combination of said lenses and said material system which separately accounts for the effects of the presence of at least said lenses by parameterized equations; and said data set of effective PSI's and DELTA's for a combination of said lenses and said material system, simultaneously evaluating actual PSI's and DELTA's for said unknown material system per se.

In the case, for instance, where the ellipsometer involved is a Rotating Analyzer, or Rotating Polarizer ellipsometer system, (but not where the ellipsometer involved is a Rotating Compensator System), it is noted that determination of "Handedness" is required. Therefore the foregoing method can include, as necessary, providing a mathematical model for said combination of said lenses and said material system which separately accounts for the retardation effects of the presence of said lenses and said material system by parameterized equations which further includes providing for the effects of Handedness. It is specifically stated that where the present invention approach of regressing onto effective PSI and DELTA values, (as determined in step b7.), is utilized, the mathematical model can be derived so that "Handedness" is accounted for in arriving at actual PSI's and DELTA's for said unknown material system per se.

As a general comment it is to be understood that separate PSI and DELTA values are achieved for each angle of incidence a beam of electromagnetic radiation makes with respect to a material substrate and for each wavelength utilized in a spectroscopic range of wavelengths.

Also, as the present invention methodology finds application in ellipsometer systems in which are present input and/or output lenses, the foregoing methods of use are recited utilizing specific reference to input and output lenses in ellipsometer systems. In general said methodology can be applied where any input and/or output optical elements are present.

Finally, while the forgoing has presented method steps in a logical to enhance disclosure, it is to be understood that the steps of any method recitation in this Specification can be practiced in any functional order and remain within the scope of the present invntion.

The present invention will be better understood by reference to the Detailed Description Section of this Disclosure, with appropriate reference being has to the Drawings.

SUMMARY OF THE INVENTION

It is a primary objective and/or purpose of the present invention to describe a lens system which enables practice of focused beam small-spot spectroscopic ellipsometry over a large wavelength range, including into the deep UV, (eg. wavelengths down to and below 190 NM). Multi-element lenses which comrpise elements made of different materials allow essentially the same focal length to be achieved over a wide wavelength range.

It is another primary objective and/or purpose of the present invention to provide methods, (as originally presented in Parent application Ser. No. 09/162,217 as regards compensating Vacuum Window Birefringence), for essentially eliminating birefringence achromatic effects of multiple element input and output lenses, (optionally in combination with other ellipsometrically indistinguishable elements), in the analysis of ellipsometric data obtained utilizing an ellipsometer system beam of electromagnetic radiation which passes through said lenses.

Other objectives and/or purposes will become apparent by reference to other sections of this Specification.

BRIEF DESCRIPTION OF THE DRAWINGS

FIG. 1a1 shows a general elemental configuration of an ellipsometer system which can be applied to investigate a material system (SS).

FIG. 1a2 shows a perspective view of another ellipsometer system configuration showing the presence of electromagnetic beam directing optical elements (PRI) and (PRO).

FIG. 1a3 shows construction of a quasi-achromatic multi-element lens which can be considered as present at AC1 or AC2 in FIG. 1a1.

FIG. 1a4 shows construction of a dual stage quasi-achromatic multi-element lens which can be considered as present at AC1 or AC2 in FIG. 1a1.

FIG. 1a5 shows a plot of spot diameter vs. wavelength which characterizes a dual stage quasi-achromatic multi-element lens as shown in FIG. 1a4, and of single stage fused silica and $CaF_2$ lenses.

FIG. 1a6 shows a plot of focal length vs. wavelength which characterizes a dual stage quasi-achromatic multi-element lens as shown in FIG. 1a4, and of single stage fused silica and $CaF_2$ lenses.

FIGS. 1a7–1a24 show various combinations of bi-concave, plano-concave, bi-convex and plano-convex lens elements which can comprise a present invention lens.

FIGS. 1a25–1a28 show various sequences of converging and diverging lens elements which can comprise a present invention dual lens system.

FIGS. 1b1–1b4 show, respectively, a positive miniscus lens; a negative miniscus lens; an aspheric convex lens and an aspheric concave lens.

FIG. 1c shows a top elevational view of the ellipsometer system of FIG. 1a2 in the region of the detector.

FIG. 2 shows a top view of the ellipsometer system of FIG. 1a2, showing the presence of optical elements (PRI) and (PRO).

FIG. 5 shows a conventional prior art ellipsometer system.

FIG. 6 shows a system, which can be used as (PRI) and/or (PRO), (shown in FIGS. 1a2 and 2), for changing the initial propagation direction of a beam of electromagnetic radiation without significantly changing the phase angle between orthogonal components thereof.

DETAILED DESCRIPTION

Figure 3A:
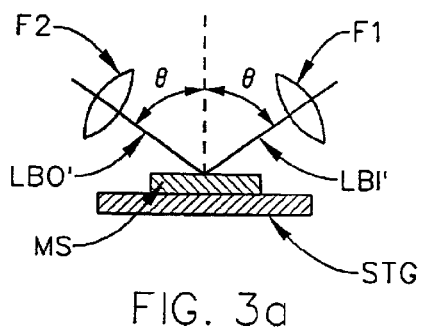
FIG. 3a shows a partial front elevational view of the ellipsometer system of FIG. 1a2.

Turning now to the Drawings, there is shown in FIG. 1a1, a general elemental configuration of an ellipsometer system to which the present invention can be applied to investigate a material system (SS). Shown for reflection and transmission are:

a. a Source of a beam electromagnetic radiation (LS);
b. a Polarizer element (P);
c. optionally a compensator element (C1);
d. (additional element(s)) (AC1);
e. a material system (SS);
f. (additional element(s)) (AC2);

g. optionally a compensator element (C2);

h. an Analyzer element (A); and i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the present invention Disclosure, primarily input and output lenses, and that only one such lens might be present in an ellipsometer system, (typically the input lens (AC1)). FIG. 1a3 shows the preferred construction of a present invention single quasi-achromatic multi-element lens which can be considered as present at AC1 or AC2. Note the presence of two (2) lens elements (FE1) and (FE3), with FE2 being, typically, a void or "air gap", or a material with functionally similar optical properties. FIG. 1a4 shows the construction of a present invention dual quasi-achromatic multi-element lens which can be considered as present at AC1 or AC2, with an element sequence of:

((DivergingD))(Converging(C))(Converging(C)) (Diverging(D)); as indicated in FIG. 1a28. In FIG. 1a4, it is to be understood that one, or both, of the two quasi-achromatic multi-element lens shown can be reversed left to right, (ie. replaced with a vertical mirror image), and remain within the scope of the present invention. Another embodiment provides that a sequence of lens elements be:

(Converging (C))(Diverging(D))(Converging(C)) (Diverging(D)); as indicated in FIG. 1a25, which is achieved by providing a vertically oriented mirror image of the first lens system which is comprised of (FE1a) (FE2a) and (FE3a) in FIG. Ia4. Other arrangements are indicated in FIGS. 1a26 and 1a27.

(Converging(C))(Diverging(D))(Diverging(D)) (Converging(C)); and (Diverging(D))(Converging(C))(Diverging(D)) (Converging(C));

And, of course, other, (not shown), configurations within the scope of the present invention include:

(ConvergingC))(Converging(C))(Diverging(D));

(Diverging(D))(Diverging(D))(Converging(C));

(Converging(C))(Diverging(D))(Diverging(D));

(Diverging(D))(Converging(C))(Diverging(D));

(Converging(C))(Converging(C))(Diverging(D)) (Diverging(D)); and (Diverging(D))(Diverging(D))(Converging(C)) (Converging(C).

It should be appreciated that the additional elements in d. can then comprise selection(s) from the group consisting of:

beam directing means, (see (PRI) (PRO) in FIG. 1a2); input lens(es); and window(s), as in a vacuum chamber; and the additional elements in f. can then comprise selection(s) from the group consisting of:

beam directing means, (see (PRI) (PRO) in FIG. 1a2);

output lens(es); and window(s), as in a vacuum chamber.

As described with respect to FIG. 1a3, at least one of the input and output lenses, (generally represented by (AC1) and (AC2) in FIG. 1a1), can, when selected and present, be of multi-element (FE1) (FE3) construction, wherein, for each of said input and output lenses (AC1) and (AC2), when selected and present, at least two elements (FE1) and (FE3) thereof are made from different materials, such that in use the focal length for each wavelength in a range of wavelengths is essentially the same as that for every other wavelength, wherein at least one of said input and output lenses, when selected and present, demonstrates properties selected from the group consisting of:

both demonstrating birefringence;

neither demonstrating birefringence;

one demonstrating birefringence and the other not.

Representative materials from which different elements in said input and output lenses can be made made are calcium fluoride (FE1) (FE1a) (FE1b), and fused silica (FE3), (FE3a) (FE3b).

Another embodiment of an ellipsometer system to which the present invention can be applied to further achieve smaller electromagnetic beam "Spot" size, is shown in FIGS. 1a2, 2 and 3a. FIG. 1a2 shows a Perspective view of a demonstrative system, FIG. 2 is a Top View, and FIG. 3a is a Front Elevational View. FIG. 1a2 shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Material System (MS) present on a Material System supporting Stage (STG). FIGS. 1a2 and 2 show that said interaction with the Surface (S) of said Material System (MS) causes a generally vertically oriented Polarized Beam of Electromagnetic Radiation (LBO') to pass through Focusing Optic (F2). FIGS. 1a2 and 2 show that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Material System (MS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

FIGS. 1b1–1b4 show, respectively, a positive miniscus lens; a negative miniscus lens; an aspheric convex lens and an aspheric concave lens. Said lens types can be utilized in the present invention at AC1 and/or AC2 and/or AC2' in FIG. 1a1; and at F1 and/or F2 in FIG. 1a2 in addition to or instead of lens configurations shown in FIGS. 1a3, 1a4 and 1a7–1a24.

FIG. 1c shows a more detailed, Top View, of a present invention Detector (DET) system as indicated in FIG. 1a2.

It is noted that (PRI) and (PRO) can be made of the same material, but the preferred embodiment provides that (PRI) be made of BK7 (refractive index approximately 1.55) and that (PRO) be made of F2 (refractive index approximately 1.7).

For demonstration purposes, FIG. 2 also shows, in dotted line form, Compensators (C) and (C'). When present one or more present Compensator(s) can be caused to rotate in use and the system is then a Rotating Compensator System and while obtaining data, both Polarizer (P) and Analyzer (A) are then held stationary. However, the Compensator(s) (C) and (C') can be absent or held stationary in use, and in use at least one of the Polarizer (P) and Analyzer (A) elements caused to rotate, thereby forming a Rotating Polarizer and/or Rotating Analyzer System. For the purposes of the present invention the specific element caused to rotate, or which is rotatable, in use is not a primary focus of Patentability. Rather, it is the presence of lenses (F1) and (F2) which provide essentially constant focal lengths over a large range of wavelengths which constitutes the improvement.

FIG. 3a shows that as viewed in frontal elevation, generally vertically oriented Polarized Beams of Electromagnetic Radiation (LBI') and (LBO') approach and are reflected from, respectively, Material System (MS) at equal angles of Incidence and Reflection ($\Theta_{I,R}$) with respect to a normal to the upper surface of said Material System (MS). It is to be noted, as demonstrated by FIG. 3b, that a generally vertically oriented Polarized Beam of Electromagnetic Radiation (LBI') caused to be incident on a Material System (MS) at Seventy-Five (75) Degrees, (a typical Brewster Angle for Semiconductors), will "Spread" so that relative dimensions of the Beam "Spot" caused to appear on said Material System (MS) are One (1) by Four (4). Where the Angle of Incidence is set to Sixty-Five (65) Degrees, FIG. 3c shows that the Spot size is shown to have relative dimensions of One (1) by Two and one-half (2.5). This demonstrates that the closer to a Normal Angle of Incidence, (eg. (θ)=zero (0.0) Degrees), with respect to a Material System (MS) surface), a generally vertically oriented Polarized Beam of Electromagnetic Radiation (LBI') is caused to assume, the more "Concentrated" will be the Beam Intensity, and the smaller will be the Material System Investigating Spot Size. Higher Beam Intensity and Reduced Material System Investigating Spot Size are often both desirable features.

Figure 3B:
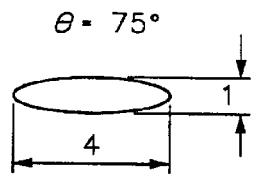
FIG. 3b shows a relative electromagnetic beam "Spot" size where an angle of incidence of seventy-five (75) degrees is utilized.
Figure 3C:
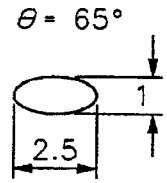
FIG. 3c shows a relative electromagnetic beam "Spot" size where an angle of incidence of sixty-five (65) degrees is utilized.

As regards the present invention, while FIGS. 3b and 3c demonstrate Beam "Spot" size reduction resulting from the control of the Angle-of-Incidence of an electromagnetic beam onto a material system, said FIGS. 3a and 3b can also be viewed and interpreted to demonstrate that at a constant angle of incidence, (whether provided by a FIG. 1a1 or FIG. 1a2 ellipsometer system configuration), different wavelengths in said Beam which pass through the Focusing Optics (AC1) (F1) can have different focal points, and the resulting "Spectral Spread" can lead to a FIG. 3b increased "Spot" size, thereby making it impossible to simultaneously, spectroscopically, investigate a small area on the substrate. An ideal situation therefore is achieved where the Focusing Optics (AC1) (F1) is achromatic, as provided by multi-element lenses such as shown in FIG. 1a3, where element (FE1) is made of a different material than is element (FE3) and where (FE2) is an air gap or equivalent. Such lenses can provide focal lengths which do not significantly change with wavelength, hence provide reduced "Spot" size. Lenses without radial symetry can also effect change as between FIGS. 3b abd 3c.

Figure 4A:
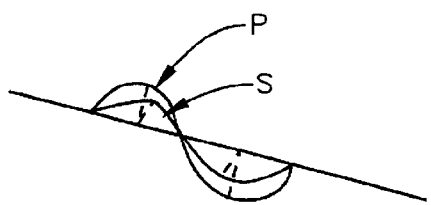
FIG. 4a shows "in-phase" components of a polarized beam of electromagnetic radiation.
Figure 4B:
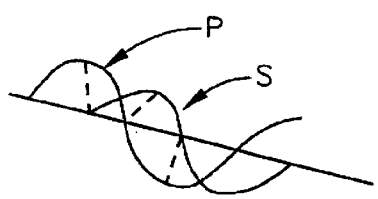
FIG. 4b shows "ninety-degree-out-of-phase" components of a polarized beam of electromagnetic radiation.
Figure 5:
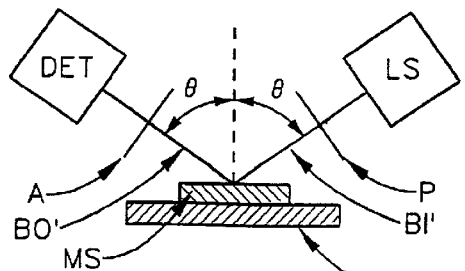
Figure 6:
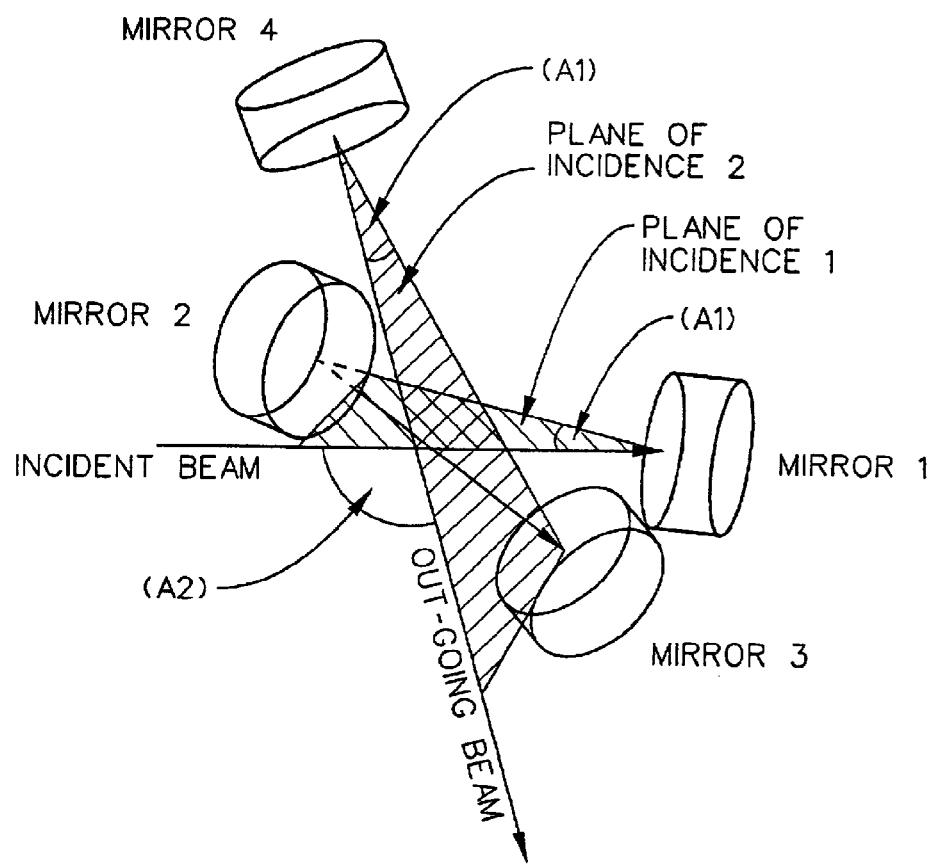

It is further noted that FIGS. 1a5 and 1a6 show plots of Spot Size and of Focal Length respectively, verses Wavelength for a Dual Quasi-Achromatic Multi-Element Lens as demonstrated in FIG. 1a4, (which can be considered as present at AC1 or AC2 in FIG. 1a1 and at F1 and/or F2 in FIG. 1a2). Shown also are curves of "Spot Size" and of "Focal Length" verses Wavelength for Fused Silica alone and for Calcium Fluoride ($CaF_2$) alone, and for a lens as shown in FIG. 1a4 where element (FE3) is Fused Silica and element (FE1) is Calcium Fluoride ($CaF_2$). Note the relatively more constant result for a multi-element lens as shown in FIG. 1a4 as compared to the results for single element lenses made from Fused Silica (FE3) and for Calcium Fluoride (FE1).

It is generally presented that achromatic lens systems, as demonstrated in FIGS. 1a3 and 1a4, are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently. Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

Continuing, for general insight, a shortcoming of Rotating Element Ellipsometer Systems, (other than Rotating Compensator Ellipsometers), generally is that certain Magnitudes of well known Material System characterizing PSI or DELTA can not be monitored thereby. For instance, in Rotating Analyzer Ellipsometer Systems, Material Systems with DELTA near zero (0.0) one-hundred-eighty (180) Degrees can not be measured. It is also noted that Thin Dielectric Films, such as Nitride and Oxide on semiconductor substrates, often present with a DELTA of one-hundred-eighty (180) Degrees at Angle of Incidence of less than the Brewster Angle, (eg. sixty-five (65) Degrees). The ellipsometer system shown in FIG. 1a2 recognizes this problem and can utilize first and/or second Optical Elements, (eg. Prisms), (PRI) and (PRO) which effect Phase Angle Retardation between "P" and "S" Orthogonal Components of a Polarized Beam of Electromagnetic Radiation caused to pass therethrough. (Note that a "P" Component of a Polarized Beam of Electromagnetic Radiation is that Component found to be in a Plane containing both an Incident Beam of Electromagnetic Radiation and a Normal to a Material System Surface, while an "S" Component is that Component perpendicular to said "P" Plane and Parallel to the Material System Surface). The Phase Angle Retardation between "P" and "S" Orthogonal Components of a Polarized Beam of Electromagnetic Radiation caused to pass therethrough can be caused to Nominally Forty-Five (45) Degrees for each Optical Element (PRI) and (PRO) shown in FIG. 2, for a total of a Nominal Ninety (90) Degrees. This added Retardation between "P" and "S" Orthogonal Components serves to shift the Material System DELTA's which a Rotating Analyzer Ellipsometer will be unable to measure to Ninety

(90) and Two-Hundred-Seventy (270) Degrees. Again, most Thin Film Material Systems present a DELTA of near zero (0.0) and one-hundred-eighty (180) Degrees, hence the first and Ads second Optical Elements (PRI) and (PRO) serve not only to direct a Polarized Beam of Electromagnetic Radiation as desired, but also serve to "Condition" said Polarized Beam of Electromagnetic Radiation so that it can be utilized to measure Material System DELTA's which are in the range of near zero (0.0) Degrees or near one-hundred-eighty (180) degrees.

While FIG. 2 shows each of the first and second Optical Elements (PRI) and (PRO) as providing a total internal reflection angle of ninety (90) degrees, so as to direct said generally vertically oriented Incident Polarized Beam of Electromagnetic Radiation (LBI') at Ninety (90) Degrees with respect to said generally horizontally oriented Polarized Beam of Electromagnetic Radiation (LBI), and so as to direct said generally horizontally oriented Polarized Beam of Electromagnetic Radiation (LBO) at Ninety (90) Degrees with respect to said generally vertically oriented Polarized Beam of Electromagnetic Radiation (LBO'), other Optical Elements which provide other Angles between Incident and internally Reflected Beams of Electromagnetic Radiation can also be adapted for use in the present invention, and said usage is within the scope of the present invention. In such a case the terminology "generally horizontally oriented" and "other than generally horizontally oriented" serves to describe the relationship between incident and reflected beams of electromagnetic radiation. As well, Optical Elements which introduce other than essentially forty-five (45) degrees of retardation between "P" and "S" components of a Polarized Beam of Electromagnetic Radiation at a point of total internal reflection can be utilized. For instance, in a Rotating Compensator Ellipsometer System, as close to zero (0.0) degrees of entered retardation at a reflection as is possible might be desirable.

It should also be recognized that the presence of first and second Optical Elements (PRI) and (PRO) allow realization of a more laterally compact Ellipsometer or Polarimeter System Design, in that, as shown in FIG. 2, the Source of Electromagnetic Radiation (LS) and Detector (DET) can be placed as shown, rather than to the Right and Left of the Material System (MS) as is typical in most Ellipsometer Systems.

FIGS. 4a and 4b show "P" and "S" Components of a Polarized Beam of Electromagnetic Radiation for both "In-Phase" and "Ninety (90) Degrees Retardation" therebetween, respectively.

FIG. 5 is included to provide a reference to conventional ellipsometer and polarimeter and the like Material System investigation systems reported in the prior art. Note that a Light Source (LS), Polarizer (P), Material System (MS) Analyzer (A) and Detector (DET) are shown, as well as Incident (BI') and Reflected (BO') Electromagnetic Radiation Beams, (which are respectively, analogically, similarly positioned as are (LBI') and (LBO') in FIG. 3a). The region of FIG. 5 in the vicinity of the Material System (MS) is very much like what is shown in FIG. 3a, but for the fact that a smaller Beam "Spot" size will be effected by a FIG. 3a system by lens (F1). Note also that the placement of the Light Source (LS) and Detector (DET) in FIG. 5 are shown to be necessarily very different from that shown in FIGS. 1a3 and 2, as the present invention first and second Optical Elements (PRI) and (PRO), shown in FIGS. 1a2 and 2, are not present. It is noted that adjustment of Light Source (LS) and Detector (DET) positioning to allow different Angles-of-Incidence (θ) to be achieved is inherently more difficult in a system fashioned after FIG. 5, (or after FIG. 1a1), than it is in a present invention system fashioned after FIGS. 1a2 and 2.

For purposes of applying the present invention methodology, in that as (PRI), (F1), (F2) and (PRO) remain stationary during use in data acquisition, it should be appreciated that the FIG. 1a2 (PRI) and Convergent Input Lens (F1) can be considered a composite system, as can (PRO) and divergent output lens (F2). The Claims should be interpreted to include ellipsometrically indistinguishable elements within the terminology "input lens" or "output lens", where applicable. (Note that the paper by Jones referenced in the Background Section of this Specification describes why birefringence from ellipsometrically indistinguishable elements can be mathematically lumped together).

Also, as shown in application Ser. No. 09/144,764, filed Aug. 31, 1998, specific beam folding optics in which specific (PRI) and (PRO) embodiments are decribed. Each of the (PRI) and (PRO) can comprise first and second systems which each comprise two pairs of reflecting means, between which first and second systems is positioned a material system. FIG. 6 shows a system, which can be used as (PRI) and/or (PRO), for changing the initial propagation direction of a beam of electromagnetic radiation without significantly changing the phase angle between orthogonal components thereof, comprises two pairs of reflecting means, (MIRROR 1) and (MIRROR 2), oriented so that said initial beam of electromagnetic radiation (INCIDENT BEAM) reflects from a first reflecting means (MIRROR 1) in the first pair of reflecting means to a second reflecting means (MIRROR 2) in said first pair of reflecting means, in a first plane, (PLANE OF INCIDENCE 1), and such that the beam of electromagnetic radiation which reflects from said second reflecting means in said first pair of reflecting means is directed to a first reflecting means (MIRROR 3) in the second pair of said reflecting means, and reflects from said first reflecting means (MIRROR 3) in said second pair of reflecting means to a second reflecting means (MIRROR 4) in said second pair of reflecting means, in a second plane (PLANE OF INCIDENCE 2), which is essentially orthogonal to said first plane; such that the direction of propagation of the beam of electromagnetic radiation reflected from the second of the reflecting means in the second pair of reflecting means is different from the propagation direction of the initial beam of electromagnetic radiation; the basis of operation being that changes entered to the phase angle between orthogonal components of a beam of electromagnetic radiation by the first of said pairs of reflecting means are effectively canceled by said second pair of reflecting means.

Allowed application Ser. No. 09/162,217 filed Sept. 29, 1998, and Allowed application Ser. No. 09/033,694 filed Mar. 3, 1998 provide additional insight, and Allowed Application Serial No. 09/144,764, filed Aug. 31, 1998 are incorporated hereinto by reference. In particular the 217 Application shows application of the present invention methodology, wherein vacuum chamber windows, at least one of which demonstrates birefringence, (instead of input and output lenses), are investigated. The 694 Application provides experimental support for operational aspects of the FIG. 1a3 ellipsometer system configuration, and the 764 Application shows specific beam folding systems.

It remains only to disclose the mathematical basis for, and derivation of, the present invention second order mathematical model corrections, and said derivation requires the use of Matracies which represent the material, and each element in the ellipsometer system.

To begin, as is disclosed in the 217 Application, it is to be understood that:

a beam of electromagnetic radiation from a source thereof can be mathematically modeled as a Stokes Vector:

$$\text{Stokes vector for unpolarized input light } I = \begin{bmatrix} 1 \\ 0 \\ 0 \\ 0 \end{bmatrix}$$

a polarization state insensitive detector can be mathematically modeled as a Stokes Vector:

Stokes vector for a polarization insensitive detector 'D': D=(1 0 0 0)

a Polarizer P, (or Analyzer A), can be mathematically modeled as Mueller Matrix:

$$\text{Mueller Matrix for a polarizer 'P' or analyzer 'A'} \quad P = \begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

Azimuthal Rotation as a function of Angle ($\phi$) effected by an element can be modeled by a Mueller Matrix:

$$R(\phi) = \begin{bmatrix} 1 & 0 & 0 & 0 \\ 0 & \cos(2\phi) & \sin(2\phi) & 0 \\ 0 & -\sin(2\phi) & \cos(2\phi) & 0 \\ 0 & 0 & 0 & 1 \end{bmatrix}$$

a Compensator, or Bi-refrinent Window or Lens with a Retardance ($\delta$) can be mathematically modeled as:

$$W(\delta) = \begin{bmatrix} 1 & 0 & 0 & 0 \\ 0 & 1 & 0 & 0 \\ 0 & 0 & \cos(\delta) & \sin(\delta) \\ 0 & 0 & -\sin(\delta) & \cos(\delta) \end{bmatrix}$$

and a Sample can be mathematically modeled by a Mueller Matrix:

$$\text{Mueller Matrix for a sample 'S':} \quad S(\Psi, \Delta) = \begin{bmatrix} 1 & -N & 0 & 0 \\ -N & 1 & 0 & 0 \\ 0 & 0 & C & S \\ 0 & 0 & -S & C \end{bmatrix}$$

where:

$N = \cos(2\Psi)$ $C = \sin(2\Psi) \cdot \cos(\Delta)$ $S = \sin(2\Psi) \cdot \sin(\Delta)$ A complete Mueller Matrix expresion for Signal Intensity out of a Rotating Analyzer ellipsometer system, without lenses (AC1) & (AC2) present, can then be written as:

Complete Mueller matrix expression for a rotating analyzer ellipsometer.

Signal_Intensity=$D \cdot (R(\cdot \phi_A) \cdot A \cdot R(\phi_A)) \cdot S \cdot (R(\cdot \phi_P) \cdot P \cdot R(\phi_P)) \cdot I$ or more explicitly as:

$$(1\ 0\ 0\ 0) \cdot \begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} \cdot \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot$$

$$\begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix} \cdot$$

$$\begin{bmatrix} 1 & -N & 0 & 0 \\ -N & 1 & 0 & 0 \\ 0 & 0 & C & S \\ 0 & 0 & -S & C \end{bmatrix} \begin{bmatrix} 1 & 0 & 0 & 0 \\ 0 & \cos(2\phi P) & -\sin(2\phi P) & 0 \\ 0 & \sin(2\phi P) & \cos(2\phi P) & 0 \\ 0 & 0 & 0 & 1 \end{bmatrix} \cdot$$

$$\begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos(2\phi P) & \sin(2\phi P) & 0 \\ 0 & -\sin(2\phi P) & \cos(2\phi P) & 0 \\ 0 & 0 & 0 & 1 \end{bmatrix} \cdot \begin{bmatrix} 1 \\ 0 \\ 0 \\ 0 \end{bmatrix}$$

Multiplying this out provides:

Signal_Intensity=$1 - \cos(2 \cdot P) \cdot N + (\cdot N + \cos(2 \cdot \phi P)) \cdot \cos(2 \cdot \phi A) + \sin(2 \cdot \phi A) \cdot C \cdot \sin(2 \cdot \phi P)$ and if the Analyzer (A) is rotating as a function of Time, (ie. $\phi A = WT$), then the abovce Detector Intensity can be written as "DC" Normalized ellipsometric ALPHA (2w) and BETA (2w) Fourier Coefficients at (2w) frequency:

$$\alpha = \frac{\cos(2 \cdot \phi P) - N}{1 - \cos(2 \cdot \phi P) \cdot N}$$

$$\beta = \frac{\sin(2 \cdot \phi P) \cdot C}{1 - \cos(2\phi P) \cdot N}$$

Where input and output lenses (AC1) and (AC2) are present, and designated as (W1) and (W2) respectively, the Signal Intensity Equation becomes:

Signal_Intensity=
$D \cdot (R(\cdot \phi_A) \cdot A \cdot R(\phi_A)) \cdot (R(\ \phi_{W2}) \cdot W(\delta 2) \cdot R(\phi_{W2})) \cdot S \cdot (R(\cdot \phi_{W1}) \cdot W(\delta 1) \cdot R(\phi_{W1})) \cdot (R(\phi_P) \cdot P \cdot R(\phi_P)) \cdot I$ Re-evaluating the Rotating Analyzer and the Detector matricies provides:
First evaluate the Rotating Analyzer and Detector Matrices:

$$D \cdot (R(\phi_A) \cdot A \cdot R(\phi_A)) = (1\ 0\ 0\ 0) \cdot \begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} \cdot$$

$$\begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix}$$

Det_Analyzer= $(1\ \cos(2 \cdot \phi A)\ \sin(2 \cdot \phi A)\ 0) = s_{out} = (s0\ s1\ s2\ s3)$ Therefore, the ALPHA (2$\phi$A) and BETA (2$\phi$A) of the complete system can be determined by multiplying out the rest of the Mueller Matricies (excluding the Analyzer and Detector Matraicies), using:

$$\alpha = \frac{s1}{s0}$$

$$\beta = \frac{s2}{s0}$$

Multiplying out the rest of the Mueller Matricies, without any present invention simplifcation provides:

$$\begin{bmatrix} 1 & 0 & 0 & 0 \\ 0 & \cos2\phi w2 & -\sin2\phi w2 & 0 \\ 0 & \sin2\phi w2 & \cos2\phi w2 & 0 \\ 0 & 0 & 0 & 1 \end{bmatrix} \cdot \begin{bmatrix} 1 & 0 & 0 & 0 \\ 0 & 1 & 0 & 0 \\ 0 & 0 & \cos\delta w2 & \sin\delta w2 \\ 0 & 0 & -\sin\delta w2 & \cos\delta w2 \end{bmatrix} \cdot$$

$$\begin{bmatrix} 1 & 0 & 0 & 0 \\ 0 & \cos2\phi w2 & \sin2\phi w2 & 0 \\ 0 & -\sin2\phi w2 & \cos2\phi w2 & 0 \\ 0 & 0 & 0 & 1 \end{bmatrix} \cdot \begin{bmatrix} 1 & -N & 0 & 0 \\ -N & 1 & 0 & 0 \\ 0 & 0 & C & S \\ 0 & 0 & -S & C \end{bmatrix} \cdot$$

-continued $$\begin{bmatrix} 1 & 0 & 0 & 0 \\ 0 & \cos2\phi w1 & -\sin2\phi w1 & 0 \\ 0 & \sin2\phi w1 & \cos2\phi w1 & 0 \\ 0 & 0 & 0 & 1 \end{bmatrix} \cdot \begin{bmatrix} 1 & 0 & 0 & 0 \\ 0 & 1 & 0 & 0 \\ 0 & 0 & \cos\delta w1 & \sin\delta w1 \\ 0 & 0 & -\sin\delta w1 & \cos\delta w1 \end{bmatrix} \cdot$$

$$\begin{bmatrix} 1 & 0 & 0 & 0 \\ 0 & \cos2\phi w1 & \sin2\phi w1 & 0 \\ 0 & -\sin2\phi w1 & \cos2\phi w1 & 0 \\ 0 & 0 & 0 & 1 \end{bmatrix} \cdot \begin{bmatrix} 1 \\ \cos2\phi P \\ \sin2\phi P \\ 0 \end{bmatrix}$$

$$t = \begin{bmatrix} s0 \\ s1 \\ s2 \\ s3 \end{bmatrix}$$

and further:

s0 =
- $1 - \cos2\phi P \cdot N \cdot \cos2\phi w1^2 - \cos2\phi P \cdot N \cdot \sin2\phi w1^2 \cdot \cos\delta w1 \ldots$
- $+ \sin2\phi P \cdot N \cdot \cos2\phi w1 \cdot \sin2\phi w1 + \sin2\phi P \cdot N \cdot \sin2\phi w1 \cdot \cos\delta w1 \cdot \cos2\phi w1$ s1 =
- $- N \cdot \cos2\phi w2 - N \cdot \sin2\phi w2 \cdot \cos\delta w2 + \cos2\phi P \cdot \cos2\phi w1^2 \cdot \cos2\phi w2^2 \ldots$
- $+ \cos2\phi P \cdot \cos2\phi w1^2 \cdot \sin2\phi w2^2 \cdot \cos\delta w2 \ldots$
- $+ \cos2\phi P \cdot \cos2\phi w1 \cdot \sin2\phi w1 \cdot C \cdot \cos2\phi w2 \cdot \sin2\phi w2 \ldots$
- $- \cos2\phi P \cdot \cos2\phi w1 \cdot \sin2\phi w1 \cdot C \cdot \sin2\phi w2 \cdot \cos\delta w2 \cdot \cos2\phi w2 \ldots$
- $+ \cos2\phi P \cdot \cos2\phi w1 \cdot \sin2\phi w1 \cdot \sin2\phi w2 \cdot \sin\delta w2 \cdot S \ldots$
- $+ \cos2\phi P \cdot \cos\delta w1 \cdot \sin2\phi w1^2 \cdot \cos2\phi w2^2 \ldots$
- $+ \cos2\phi P \cdot \cos\delta w1 \cdot \sin2\phi w1^2 \cdot \sin2\phi w2^2 \cdot \cos\delta w2 \ldots$
- $- \cos2\phi P \cdot \sin2\phi w1 \cdot \cos\delta w1 \cdot \cos2\phi w1 \cdot C \cdot \cos2\phi w2 \cdot \sin2\phi w2 \ldots$
- $+ \cos2\phi P \cdot \sin2\phi w1 \cdot \cos\delta w1 \cdot \cos2\phi w1 \cdot C \cdot \sin2\phi w2 \cdot \cos\delta w2 \cdot \cos2\phi w2 \ldots$
- $- \cos2\phi P \cdot \sin2\phi w1 \cdot \cos\delta w1 \cdot \cos2\phi w1 \cdot \sin2\phi w2 \cdot \sin\delta w2 \cdot S \ldots$
- $+ \cos2\phi P \cdot \sin2\phi w1 \cdot \sin\delta w1 \cdot S \cdot \cos2\phi w2 \cdot \sin2\phi w2 \ldots$
- $- \cos2\phi P \cdot \sin2\phi w1 \cdot \sin\delta w1 \cdot S \cdot \sin2\phi w2 \cdot \cos\delta w2 \cdot \cos2\phi w2 \ldots$
- $- \cos2\phi P \cdot \sin2\phi w1 \cdot \sin\delta w1 \cdot \sin2\phi w2 \cdot \sin\delta w2 \cdot C \ldots$
- $+ \sin2\phi P \cdot \sin2\phi w1 \cdot \cos2\phi w1 \cdot \cos2\phi w2^2 \ldots$
- $+ \sin2\phi P \cdot \sin2\phi w1 \cdot \cos2\phi w1 \cdot \sin2\phi w2^2 \cdot \cos\delta w2 \ldots$
- $+ \sin2\phi P \cdot \sin2\phi w1^2 \cdot C \cdot \cos2\phi w2 \cdot \sin2\phi w2 \ldots$
- $- \sin2\phi P \cdot \sin2\phi w1^2 \cdot C \cdot \sin2\phi w2 \cdot \cos\delta w2 \cdot \cos2\phi w2 \ldots$
- $+ \sin2\phi P \cdot \sin2\phi w1^2 \cdot \sin2\phi w2 \cdot \sin\delta w2 \cdot S \ldots$
- $- \sin2\phi P \cdot \cos2\phi w1 \cdot \cos\delta w1 \cdot \sin2\phi w1 \cdot \cos2\phi w2^2 \ldots$
- $- \sin2\phi P \cdot \cos2\phi w1 \cdot \cos\delta w1 \cdot \sin2\phi w1 \cdot \sin2\phi w2^2 \cdot \cos\delta w2 \ldots$
- $+ \sin2\phi P \cdot \cos\delta w1 \cdot \cos2\phi w1^2 \cdot C \cdot \cos2\phi w2 \cdot \sin2\phi w2 \ldots$
- $- \sin2\phi P \cdot \cos\delta w1 \cdot \cos2\phi w1^2 \cdot C \cdot \sin2\phi w2 \cdot \cos\delta w2 \cdot \cos2\phi w2 \ldots$
- $+ \sin2\phi P \cdot \cos\delta w1 \cdot \cos2\phi w1^2 \cdot \sin2\phi w2 \cdot \sin\delta w2 \cdot S \ldots$
- $- \sin2\phi P \cdot \cos2\phi w1 \cdot \sin\delta w1 \cdot S \cdot \cos2\phi w2 \cdot \sin2\phi w2 \ldots$
- $+ \sin2\phi P \cdot \cos2\phi w1 \cdot \sin\delta w1 \cdot S \cdot \sin2\phi w2 \cdot \cos\delta w2 \cdot \cos2\phi w2 \ldots$
- $+ \sin2\phi P \cdot \cos2\phi w1 \cdot \sin\delta w1 \cdot \sin2\phi w2 \cdot \sin\delta w2 \cdot C$ s2 =
- $- \cos2\phi w2 \cdot \sin2\phi w2 \cdot N + \cos2\phi w2 \cdot \sin2\phi w2 \cdot N \cdot \cos\delta w2 \ldots$
- $+ \cos2\phi P \cdot \cos2\phi w1^2 \cdot \cos2\phi w2 \cdot \sin2\phi w2 \ldots$
- $- \cos2\phi P \cdot \cos2\phi w1^2 \cdot \sin2\phi w2 \cdot \cos\delta w2 \cdot \cos2\phi w2 \ldots$
- $+ \cos2\phi P \cdot \cos2\phi w1 \cdot \sin2\phi w1 \cdot C \cdot \sin2\phi w2^2 \ldots$
- $+ \cos2\phi P \cdot \cos2\phi w1 \cdot \sin2\phi w1 \cdot C \cdot \cos2\phi w2^2 \cdot \cos\delta w2 \ldots$
- $- \cos2\phi P \cdot \cos2\phi w1 \cdot \sin2\phi w1 \cdot \cos2\phi w2 \cdot \sin\delta w2 \cdot S \ldots$
- $+ \cos2\phi P \cdot \cos\delta w1 \cdot \sin2\phi w1^2 \cdot \cos2\phi w2 \cdot \sin2\phi w2 \ldots$
- $- \cos2\phi P \cdot \cos\delta w1 \cdot \sin2\phi w1^2 \cdot \sin2\phi w2 \cdot \cos\delta w2 \cdot \cos2\phi w2 \ldots$
- $+ \cos2\phi P \cdot \sin2\phi w1 \cdot \cos\delta w1 \cdot \cos2\phi w1 \cdot C \cdot \sin2\phi w2^2 \ldots$
- $+ \cos2\phi P \cdot \sin2\phi w1 \cdot \cos\delta w1 \cdot \cos2\phi w1 \cdot C \cdot \cos2\phi w2^2 \cdot \cos\delta w2 \ldots$
- $- \cos2\phi P \cdot \sin2\phi w1 \cdot \cos\delta w1 \cdot \cos2\phi w1 \cdot \cos2\phi w2 \cdot \sin\delta w2 \cdot S \ldots$
- $+ \cos2\phi P \cdot \sin2\phi w1 \cdot \sin\delta w1 \cdot S \cdot \sin2\phi w2^2 \ldots$
- $+ \cos2\phi P \cdot \sin2\phi w1 \cdot \sin\delta w1 \cdot S \cdot \cos2\phi w2^2 \cdot \cos\delta w2 \ldots$
- $+ \cos2\phi P \cdot \sin2\phi w1 \cdot \sin\delta w1 \cdot \cos2\phi w2 \cdot \sin\delta w2 \cdot C \ldots$
- $+ \sin2\phi P \cdot \sin2\phi w1 \cdot \cos2\phi w1 \cdot \cos2\phi w2 \cdot \sin2\phi w2 \ldots$
- $- \sin2\phi P \cdot \sin2\phi w1 \cdot \cos2\phi w1 \cdot \sin2\phi w2 \cdot \cos\delta w2 \cdot \cos2\phi w2 \ldots$
- $+ \sin2\phi P \cdot \sin2\phi w1^2 \cdot C \cdot \sin2\phi w2^2 \ldots$
- $+ \sin2\phi P \cdot \sin2\phi w1^2 \cdot C \cdot \cos2\phi w2^2 \cdot \cos\delta w2 \ldots$
- $- \sin2\phi P \cdot \sin2\phi w1^2 \cdot \cos2\phi w2 \cdot \sin\delta w2 \cdot S \ldots$
- $- \sin2\phi P \cdot \cos2\phi w1 \cdot \cos\delta w1 \cdot \sin2\phi w1 \cdot \cos2\phi w2 \cdot \sin2\phi w2 \ldots$
- $+ \sin2\phi P \cdot \cos2\phi w1 \cdot \cos\delta w1 \cdot \sin2\phi w1 \cdot \sin2\phi w2 \cdot \cos\delta w2 \cdot \cos2\phi w2 \ldots$ -continued + $\sin2\phi P \cdot \cos\delta w1 \cdot \cos2\phi w1^2 \cdot C \cdot \sin2\phi w2^2$ ...
+ $\sin2\phi P \cdot \cos\delta w1 \cdot \cos2\phi w1^2 \cdot C \cdot \cos2\phi w2^2 \cdot \cos\delta w2$ ...
+ - $\sin2\phi P \cdot \cos\delta w1 \cdot \cos2\phi w1^2 \cdot \cos2\phi w2 \cdot \sin\delta w2 \cdot S$ ...
+ - $\sin2\phi P \cdot \cos2\phi w1 \cdot \sin\delta w1 \cdot S \cdot \sin2\phi w2^2$ ...
+ - $\sin2\phi P \cdot \cos2\phi w1 \cdot \sin\delta w1 \cdot S \cdot \cos2\phi w2^2 \cdot \cos\delta w2$ ...
+ - $\sin2\phi P \cdot \sin\delta w1 \cdot \cos2\phi w1 \cdot \cos2\phi w2 \cdot \sin\delta w2 \cdot C$ with ellipsometric ALPHA and BETA being given by:

$$\alpha = \frac{s1}{s0}$$

$$\beta = \frac{s2}{s0}$$

Now, the present invention simplification is mathematically based on the fact that input and output rotation matrices involve Sin and Cos of double the rotation angle imposed thereby, and that if an angle of forty-five (45) degrees is assumed for that rotation angle, then the Sin(2×45) becomes 1.0, and the Cos(2×45) becomes 0.0. This assumption is equivalent to saying that birefringence introduced by each of said input and output lenses can be split into two orthogonal components, and that one of said orthogonal components is oriented "In-The-Plane" of the beam of electromagnetic radiation as it interacts with a material system, and that the other orthogonal component is oriented "Out-Of-The-Plane" of the beam of electromagnetic radiation as it interacts with a material system. When this assumption is made, the following hold:

for the "In-Plane" orthogonal component:

for in-plane, $\cos2\phi w1 = \cos2\phi w2 = 1$, $\sin2\phi w1 = \sin2\phi w2 = 0$ $$s0 = 1 - \cos2\phi P \cdot N$$

$$s1 = \cos2\phi P - N$$

$$s2 = ((-\cos\delta w1 \cdot \sin\delta w2 - \sin\delta w1 \cdot \cos\delta w2) \cdot S + (\cos\delta w1 \cdot \cos\delta w2 - \sin\delta w1 \cdot \sin\delta w2) \cdot C) \cdot \sin2\phi P$$

$$s2 = \sin2\phi P \cdot (\cos(\delta w1 + \delta w2) \cdot C - \sin(\delta w1 + \delta w2) \cdot S)$$

$$s2 = \sin2\phi P \cdot \sin(2\Psi) \cdot \cos(\Delta + \delta w1 + \delta w2)$$

$$\alpha = \frac{\cos2\phi P - N}{1 - \cos2\phi P \cdot N}$$

$$\beta = \frac{\sin2\phi \cdot \sin(2\Psi) \cdot \cos(\Delta + \delta w1 + \delta w2)}{1 - \cos2\phi P \cdot N}$$

for the "Out-Of-Plane" orthogonal component:

for out-of-plane, $\cos2\phi w1 = \cos2\phi w2 = 0$, $\sin2\phi w1 = \sin2\phi w2 = 1$ $$s0 = 1 - \cos2\phi P \cdot N \cdot \cos\delta w1$$

$$s1 = \cdot N \cdot \cos\delta w2 - \cos2\phi P \cdot \sin\delta w1 \cdot \sin\delta w2 \cdot C + \sin2\phi P \cdot \sin\delta w2 \cdot S + \cos2\phi P \cdot \sin\delta w1 \cdot \cos\delta w2$$

$$s2 = \cos2\phi P \cdot \sin\delta w1 \cdot S - \sin2\phi P \cdot C$$

$$\alpha = \frac{\cdot N \cdot \cos\delta w2 - \cos2\phi P \cdot \sin\delta w1 \cdot \sin\delta w2 \cdot C + \sin2\phi P \cdot \sin\delta w2 \cdot S - \cos2\phi P \cdot \cos\delta w1 \cdot \cos\delta w2}{1 - \cos2\phi P \cdot N \cdot \cos\delta w1}$$

$$\beta = \frac{\cos2\phi P \cdot \sin\delta w1 \cdot S - \sin2\phi P \cdot C}{1 - \cos2\phi P \cdot N \cdot \cos\delta w1}$$

(Note that the immediately foregoing Equations become "exact" if the mathematical model allows input-polarizer and output-analyzer azimuthal angles to vary slightly).

It will be appreciated that the equations for ellipsometric ALPHA and BETA with the present invention simplifying assumption are greatly simplified as compared to the equations for ellipsometric ALPHA and BETA without the present invention simplifying assumption being made. In addition, said simplified equations for ellipsometric ALPHA and BETA provide second order mathematical model correction. And, said present invention second order mathematical model correction equations are of approximately the same level of complexity as are the equations which provide first order mathematical model correction, which, as found in the literature are:

$$\alpha = \frac{\cos2\phi P - N}{1 - \cos2\phi P \cdot N} \ldots + \frac{\sin2\phi P \cdot \sin2\phi w2 \cdot \delta w2 \cdot S}{1 - \cos2\phi P \cdot N}$$

$$\beta = \frac{\sin2\phi P \cdot \cos(\Delta + \cos2\phi w2 \cdot \delta w2 + \cos2\phi w1 \cdot \delta w1)}{1 - \cos2\phi P \cdot N} \ldots + \frac{\sin2\phi w1 \cdot \delta w1 \cdot \cos2\phi P \cdot S}{1 - \cos2\phi P \cdot N}$$

the application of which are shown by FIGS. 4a, 4b and 4c in Parent application Ser. No. 09/162,217. Again, for comparison, it is emphasized that FIGS. 6a, 6b and 6c of Parent application Ser. No. 09/162,217 present results of application of the present invention second order mathematical model correction equations when vacuum chamber windows were investigated.

It is to be further understood that the present invention applies parameterized equations for retardance ($\Delta$) of input and output lenses of the form:

Delta Offset($\lambda$)=DelOff1/$\lambda$(1+DelOff2/$\lambda^2$+DelOff3/$\lambda^4$)

As presented in the Disclosure of the Invention Section of this Disclosure, the present invention includes application of said parameterized equations for input and output lens retardance, both in conjunction with, and without, the present invention simplifying assumption that input and output lenses rotation matrices, which involve the Sin(2θ)

and Cos($2\psi$) of double the rotation angle imposed thereby, have an angle of forty-five (45) degrees assumed for that rotation angle, so that the Sin becomes 1.0, and the Cos becomes 0.0. This assumption, it is to be understood, provides that each orthogonal component of the birefringence of both input and output lenses, and associated ellipsometrically indistinguishable components is is to be treated separately, with net retardance entered between said orthogonal components by a beam of electromagnetic radiation by passage through an input and/or output lens is determined by a comparison of the separate effects on each of said orthogonal components. It is noted that while the present invention mathematical justification for the simplifying assumption is based upon assuming an angle of forty-five (45) degrees for the rotation angle imposed by a input or output lens, so that the Sin becomes 1.0, and the Cos becomes 0.0, the concept behind the present invention simplifying assumption is that orthogonal components of lens/associated indistinguishable components can be considered to each be separately represented by a parameterized retardance equation. When the assumption of angle of forty-five (45) degrees for the rotation angle is made, however, the result is that one orthogonal component is out of the plane of incidence of a beam of electromagnetic radiation which is caused to interact with a material system, and one orthogonal component thereof is in said plane of incidence. This, of course, means that where a material can not be provided a parameterized equation for retardance, correlation of retardance entered by the input and output lenses "in-plane", and that of a material system, will exist, and must be broken. Said "in-plane" correlation can be broken by providing a material system that can be parameterized, and simultaneously evaluating parameters in it, and in parameterized equations for retardance of the input and output lenses in a separate calibration procedure.

While the preceding approach works well for analyzing ellipsometric data acquired by a Rotating Analyzer or Rotating Polarizer ellipsometer system wherein lenses are present, it is further to be understood that in cases where it is important to extract "true" values for the PSI and DELTA of a material system, (eg. during material deposition), additional mathematics is required. The following equations are derived by algebraically inverting the previous equations, and transforming the effective PSI and DELTA measured in the presence of lenses into true PSI and DELTA values of a material system:

$C2P = \cos 2\phi P; S2P = \sin 2\phi P; C2A = \cos 2\phi A; S2A = \sin 2\phi A$ $Nwineff = \cos(2 \cdot \Psi wineff)$ $Cwineff = \sin(2 \cdot \Psi wineff) \cdot \cos(\Delta wineff)$ $Swineff = \pm \sin(2 \cdot \Psi wineff) \cdot \sin(\Delta wineff)$ $s1 = \dfrac{(C2P - Nwineff)}{1 - Nwineff \cdot C2P}$ $s2 = \dfrac{Cwineff \cdot S2P}{1 - Nwineff \cdot C2P}$ $s3 = \dfrac{-Swineff \cdot S2P}{1 - Nwineff \cdot C2P}$ $a = (\cos\delta w2 \cdot s1 + \sin\delta w2 \cdot s3)$ -continued $b = s2$ $c = -(\sin\delta w2 \cdot s1 - \cos\delta w2 \cdot s3)$ $Ntrue = \dfrac{(a - \cos\delta w1 \cdot C2P)}{(a \cdot \cos\delta w1 \cdot C2P - 1)}$ $Ctrue = \dfrac{(c \cdot \sin\delta w1 \cdot C2P + S2P \cdot b) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$ $Strue = \dfrac{(b \cdot \sin\delta w1 \cdot C2P - S2P \cdot c) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$ $\Psi true = \mathrm{acos}(Ntrue) \cdot 0.5$ $\Delta true = \mathrm{atan2}(Strue, Ctrue) - DeltaOffset$ Two roots are calculated by the choosing the sign of the "Swineff" term. Note that when the lens correction terms ($\delta w_1$) and ($\delta w_2$) are zero (0.0), the two roots reduce to ($+/-\Delta$), the expected ambiguity for a Rotating Analyzer ellipsometer system.

Continuing, where a Rotating Compensator ellipsometer system is present, use of the same Mueller matrix formalism as for the Rotating Analyzer ellipsometer system, the Fourier coefficients for the Rotating Compensator ellipsometer system can also be derived. The same orthogonalization approach to deriving second order lens effects was utilized, (ie. setting the fast axis of lens birefringence to forty-fve (45) degrees), to determine the out-of-plane lens birefringence, with the in-plane component being added directly to material system DELTA. (Note, in the following equations the ($\delta$) is the retardance of the compensator system.

$$DC = \left[\dfrac{1}{2} \cdot (1 + \cos\delta) \cdot \begin{pmatrix} -C2P \cdot \cos\delta w1 \cdot N + C2P \cdot \cos\delta w1 \cdot \\ C2A \cdot \cos\delta w2 \ldots + C2P \cdot \sin\delta w1 \cdot S2A \cdot S - \\ C2P \cdot \sin\delta w1 \cdot C2A \cdot \sin\delta w2 \cdot C \ldots + \\ S2P \cdot S2A \cdot C + S2P \cdot C2A \cdot \sin\delta w2 \cdot S \end{pmatrix}\right] \ldots +$$

$1 - C2A \cdot \cos\delta w2 \cdot N$ $\alpha 2 = \left(\dfrac{\sin\delta w1 \cdot N - \sin\delta w1 \cdot C2A \cdot \cos\delta w2 \ldots +}{\cos\delta w1 \cdot S2A \cdot S - \cos\delta w1 \cdot C2A \cdot \sin\delta w2 \cdot C}\right) \cdot \sin\delta \cdot S2P$ $\beta 2 = \left(\dfrac{-\sin\delta w1 \cdot N + \sin\delta w1 \cdot C2A \cdot \cos\delta w2 \ldots +}{-\cos\delta w1 \cdot S2A \cdot S + \cos\delta w1 \cdot C2A \cdot \sin\delta w2 \cdot C}\right) \cdot \sin\delta \cdot C2P$ $\alpha 4 = \dfrac{1}{2} \cdot (r - \cos\delta) \cdot$ $\begin{pmatrix} -C2P \cdot \cos\delta w1 \cdot N + C2P \cdot \cos\delta w1 \cdot C2A \cdot \cos\delta w2 \ldots + \\ C2P \cdot \sin\delta w1 \cdot S2A \cdot S - C2P \cdot \sin\delta w1 \cdot C2A \cdot \sin\delta w2 \cdot C \ldots + \\ -S2P \cdot S2A \cdot C - S2P \cdot C2A \cdot \sin\delta w2 \cdot S \end{pmatrix}$ $\beta 4 = \dfrac{1}{2} \cdot (1 - \cos\delta) \cdot$ $\begin{pmatrix} C2P \cdot S2A \cdot C + C2P \cdot C2A \cdot \sin\delta w2 \cdot S - S2P \cdot \cos\delta w1 \cdot N \ldots + \\ S2P \cdot \cos\delta w1 \cdot C2A \cdot \cos\delta w2 \ldots + \\ S2P \cdot \sin\delta w1 \cdot S2A \cdot S - S2P \cdot \sin\delta w1 \cdot C2A \cdot \sin\delta w2 \cdot C \end{pmatrix}$ As in the Rotating Analyzer or Rotating Polarizer ellipsometer system case, a global regression calibration can be used to find the Rotating Compensator ellipsometer system calibration parameter values, in addition to out-of-plane lens parameterized equation values. And as described previously herein for the Rotating Analyzer ellipsometer system, a standard model fit with a parameterizable material in place can be carried out to determine values for parameters in-plane.

It is noted that an advantage of the Rotating Compensator ellipsometer system is that it can correctly measure ellipsometric DELTAS over the full range of zero (0.0) to three-hundred-sixty (360) degrees. This implies that the true PSI and DELTA parameters can be directly inverted at data acquisition time from the measured Fourier Coefficients (ie. ALPHA and BETA), assuming that parameters in parametric lens correction equations for retardance have been previously determined. The inversion equations are:

$$\Psi = \frac{1}{2} \cdot \operatorname{atan}\left[\frac{\left(\sqrt{\left[\frac{(\cos\delta w1 \cdot (1-\cos\delta) \cdot (-S2P \cdot a2 + C2P \cdot b2)) \ldots +}{2 \cdot \sin\delta \cdot \sin\delta w1 \cdot (a4-C2P+b4 \cdot S2P)}\right]^2 \ldots + 4(-a4 \cdot S2P + C2P \cdot b4)^2}\right)}{\left[(2 \cdot \cos\delta w1 \cdot (a4 \cdot C2P + b4 \cdot S2P)) \ldots + \frac{(1-\cos\delta)}{\sin\delta} \cdot \sin\delta w1 \cdot (S2P \cdot a2 - C2P \cdot b2)\right]}\right]$$

$$\Delta = \left[\operatorname{atan2}\left[\left[\frac{((1-\cos\delta) \cdot \cos\delta w1 \cdot (b2 \cdot C2P - a2 \cdot S2P)) \ldots +}{2 \cdot \sin\delta \cdot \sin\delta w1 \cdot (a4 \cdot C2P + b4 \cdot S2P)}\right] \cdot 2 \cdot \sin\delta \cdot (b4 \cdot C2P - a4 \cdot S2P)\right]\right] \ldots + \text{Delta\_Offset}$$

It is noted that, with a bit of algebra, all the equations for the Rotating Compensator ellipsometer system can be reduced to first order expressions as given in the Kleim et al. reference cited in the Background Section.

In summary, the present invention discloses that multi-element lenses can be produced that provide essentially constant focal lengths and small spot size over a large spectroscopic range of wavelengths, and that said multi-element lenses can be produced which demonstrate small birefringence. The present invention also teaches, however, that any birefringent effects presented by a present invention multi-element lenses, (and any ellipsometically non-distinguishable adjacent elements such as vacuum system windows and/or beam directing means), can be de-correlated from material system PSI and DELTA results, by practice of a methodology originally developed for acquiring ellipsometric data through vacuum chamber windows and initially disclosed in Parent application Ser. No. 09/162,217. The key insight enabling said accomplishment is that lens bi-refringence can be split into "out-of-plane" and "in-plane" components, where the "plane" referred to is the plane of incidence of an electromagnetic beam of radiation with respect to a material system. Splitting the lens birefringence into said orthogonal components allowed derivation of second order lens corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a material system DELTA. A separate step, utilizing a material system for which retardance can be modeled by a parameterized equation, allows evaluation of the parameters in parametric equations for the "in-plane" components of lenses separately. Work reported in the literature by other researchers regarding analogically similar window corrections provided equations which corrected only first order effects, and said equations have proven insufficient to correct for large, (eg. six (6) degrees), of retardance. (It is noted that prior work with respect to vacuum window corrections, orthogonal components were derived with respect to window fast axes, which is offset from the material system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a material system DELTA parameter unless a global regression fit using a parameterizable material system is performed at calibration time.

The present invention methodology comprising two steps disclosed herein, fully and unambiguously determines lens correction terms.

After parameters in parameterized equations for retardance are evaluated by the method of the present invention, ellipsometric data can be taken through lenses, (eg. input and output), and said data can be quickly and accurately analyzed by applying the correction factors in a mathematical model for a material system, (in the case where a Rotating Analyzer ellipsometer system was used to acquire data), or the lens effects can be simply quantitatively subtracted away to yield "true" ellipsometric PSI and DELTA values, (in the case where a Rotating Compensator ellipsometer system was used to acquire data).

It is to be appreciated that the correlation breaking methodology of the present invention is substantially the same as that disclosed in the Parent application, Ser. No. 09/162,217 filed Sep. 29, 1998, with the difference being that the present invention provides compensation to input, and output, lenses, (perhaps in combination with beam directing optics), rather than, or in addition to, to vacuum chamber windows, (which can be present as mathematically lumped-in with FIG. 1a1 (AC1) and (AC2) input and output lenses, as described by the Jones reference disclosed in the Background Section). It is also noted that while achromatic multi-element input and output lenses are preferred for application in the present invention, any lenses can be applied where correlation breaking techniques are applied.

It is generally noted that the terminology "positive" or "+" as used to identify a lens means it is converging, whereas the terminology "negative" or "−", as used to identify a lens means it is diverging.

It is emphasized that a system of spatially separated input and output lenses can provide that at least one lens which is not significantly birefringent is selected from the group consisting of: (essentially a surrounding ambient; and a multi-element lens). That is, it is within the scope of the present invention to interpret simple ambient atmosphere as being an input or output lens, and where Claims recite the providing of separated input and output lenses, it should be kept in mind that one of said input and output "lenses" can be effectively the effective absence of any per se. lens. In that light it is emphasized that a present invention ellipsometer system can include a focusing input lens but not an output lens and be an acceptable present invention configuration. That is, while the foregoing disclosure often alludes to the presence of both input and output lenses, said language is to be interpreted generally to include cases wherein only one of said lenses is present, and the other lens is but ambient atmosphere.

It is to be understood that the foregoing presented numerous specific examples of lenses and systems which are non-limiting. For instance, where Claims do not recite specific lens construction, any functional lens construction is to be considered within the scope thereof. That is, while FIGS. 1a3, 1a4 and 1a7–1a28 show lens constructions which are preferred, said specific examples are not to be intepreted as limiting in, for instance, Method Claims for accurately evaluating parameters in parameterized equations in a mathematical model of a system of spatially separated input and output optical elements. Claims which do not recite specific lens construction are not to be read as limited by specific examples shown, where functional equivalents can be successfully applied. For instance, it is specifically noted that either void region, FE2a or FE2b, in FIG. 1a4 can be absent, as where elements FE1a and FE3a make direct contact over their mid-region, and/or where FE1b and FE3b make direct contact over their mid-region thereof. This can occur, for instance, where the convex curvature of lens element FE1a is the same as the concave curvature of element FE3a in FIG. 1a3. Additionally, while preferred lenses applied in the present invention, as shown in FIG. 1a3, comprise two elements, where specific lens construction is not recited in a Claim, it is to be understood that any number of, and type of, elements can comprise a lens, (eg. comprise more than two elements, comprise meniscus and/or aspheric elements with radial or non-radial symetry).

It is further specifically noted that while the lenses shown in FIGS. 1a3, 1a4 and 1a7–1a28 are typically selected to demonstrate radial symetry, it is within the scope of the present invention to utilize non-radially symetric lenses, where, for instance, a spot size length to width aspect ratio is to be modified thereby. Therefore any lens shown or indicated in FIGS. 1a3, 1a4 and 1a7–1a28 can be designed to demonstrate radial symetry, or non-radial symetry, or be of any other functional type, where the achromatic properties are present.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for monitoring change in:
    the ratio of and/or
    the phase between orthogonal components in;
    a polarized beam of electromagnetic radiation which is caused by interaction with a material system;
    said system comprising input and output lenses which are each of multiple element construction, wherein, for each of said input and output lenses at least two elements thereof are made from different materials, such that in use the focal length for each wavelength in a range of wavelengths is within an acceptable range of focal lengths, wherein said input and output lenses are characterized by a selection from the group consisting of:
    both demonstrate birefringence; and
    one thereof demonstrates birefringence and the other not.

2. A system as in claim 1, wherein said input and output lenses each comprises two sequentially oriented elements, one of said two sequentially oriented elements being of a shape and orientation which individually diverges a beam of electromagnetic radiation caused to pass therethrough, and the other being of a shape and orientation which individually converges a beam of electromagnetic radiation caused to pass therethrough, wherein said convergence effect is greater than said divergence effect; there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation.

3. A system as in claim 1, wherein at least one of said input and output lens system comprises:
    a sequential combination of a bi-convex element and a bi-concave element.

4. A system as in claim 1, wherein at least one of said input and output lens system comprises:
    a sequential combination of a bi-concave element and a bi-convex element.

5. A system as in claim 1, wherein at least one of said input and output lens system comprises:
    a sequential combination of a bi-convex element and a plano-concave element with said concave side of said plano-concave element adjacent to said bi-convex element.

6. A system as in claim 1, wherein at least one of said input and output lens system comprises:
    a sequential combination of a bi-convex element and a plano-concave element with said essentially flat side of said plano-concave element being adjacent to said bi-convex element.

7. A system as in claim 1, wherein at least one of said input and output lens system comprises:
    a sequential combination of a plano-concave element and a bi-convex element with said essentially flat side of said plano-concave element adjacent to said bi-concave element.

8. A system as in claim 1, wherein at least one of said input and output lens system comprises:
    a sequential combination of a plano-concave element and bi-convex element with said concave side of said plano-concave element adjacent to said bi-convex element.

9. A system as in claim 1, wherein at least one of said input and output lens system comprises:
    a sequential combination of a plano-convex element and a bi-concave element with said essentially flat side of said plano-convex element adjacent to said bi-concave element.

10. A system as in claim 1, wherein at least one of said input and output lens system comprises:
    a sequential combination of a bi-concave element with a plano-convex element with said convex side of said plano-convex element adjacent to said bi-concave element.

11. A system as in claim 1, wherein at least one of said input and output lens system comprises:

a sequential combination of a plano-concave element and a plano-convex element with the essentially flat side of said plano-concave element being adjacent to the convex side of the plano-convex element.

12. A system as in claim 1, wherein at least one of said input and output lens system comprises:

a sequential combination of a plano-concve element and a plano-convex element with the essentially flat side of said planoconcave element being adjacent tot he convex side of said plano-convex element.

13. A system as in claim 1, wherein at least one of said input and output lens system comprises:

a sequential combination of a plano-convex element and a plano-concave element with the essentially flat side of said plano-covex element and the essentially flat side of said plano-concave element being adjacent to one another.

14. A system as in claim 1, wherein at least one of said input and output lens system comprises:

a sequential combination of a plano-concave element and a plano-convex element with the concave side of said plano-concave element being adjacent to the convex side of the plano-convex element.

15. A system as in claim 1, wherein at least one of said input and output lens system comprises:

a sequential combination of a plano-convex element and a bi-concave element with said convex side of said plano-convex element adjacent to said bi-concave element.

16. A system as in claim 1, wherein at least one of said input and output lens system comprises:

a sequential combination of a bi-concave element and a plano-convex element with said essentially flat side of said plano-convex element adjacent to said bi-concave element.

17. A system as in claim 1, wherein at least one of said input and output lens system comprises:

a sequential combination of a plano-convex element and a plano-concave element with said convex side of said plano-convex element adjacent to the concave side of the plano-concave element.

18. A system as in claim 1, wherein at least one of said input and output lens system comprises:

a sequential combination of a plano-concave element and a plano-convex element with said essentially flat side of said plano-convex element being adjacent to the essentially flat side of the plano-concave element.

19. A system as in claim 1, wherein at least one of said input and output lens system comprises:

a s quential combination of a plano-convex element and a plano-concave element with said convex side of said plano-convex element being adjacent to the essentially flat side of the plano-concave element.

20. A system as in claim 1, wherein at least one of said input and output lens system comprises:

a sequential combination of a plano-concave element with a plano-convex element with the essentially flat side of said plano-convex element being adjacent to the concave side of said plano-concave element.

21. An system as in claim 1, characterized by at least one condition selected from the group consisting of:

at least one of the input and output lenses comprises at least two sequentially oriented elements, and is characterized by being a selection from the group consisting of:

a sequential combination of a converging element and a diverging element;

a sequential combination of a diverging element and a converging element;

a sequential combination of a converging element, a diverging element, a converging element and a diverging element;

a sequential combination of a converging element, a diverging element, a diverging element and a converging element;

a sequential combination of a diverging element, a converging element, a diverging element and a converging element;

a sequential combination of a diverging element, a converging element, a converging element and a diverging element;

includes a miniscus lens; and includes an aspherical lens.

22. A system as in claim 1, wherein at least one of said input and output lens system comprises two elements with a region therebetween, wherein said region between said at least two elements has the optical properties of a selection from the group consisting of:

a void region; and a functional equivalent to a void region.

23. A system as in claim 1, wherein for each of the input and output lenses, each of said at least two elements thereof are made from different materials independently selected from the group consisting of:

$CaF_2$;

$BaF_2$;

LiF;

$MgF_2$; and fused silica;

and wherein each of said at least two elements are individually selected to be made of different materials.

24. A system as in claim 1, wherein at least one of the input and output lenses is characterized by at least one selection from the group consisting of:

a) the focal length is between forty and forty-one millimeters over a range of wavelengths of at least two-hundred to seven-hundred nanometers;

b) the focal length varies by less than five (5%) percent over a range of wavelengths of between two-hundred and five-hundred nanometers; and c) the spot diameter at the focal length is less than seventy-five microns over a range of wavelengths of at least two-hundred to seven-hundred nanometers.

25. A system as in claim 1, wherein one of said input and output lenses comprises an element made of a selection from the group consisting of:

$CaF_2$; and fused silica.

26. A system as in claim 1, in which at least one of said input and output lens is made of two elements, one of said elements being made of fused silica and the other of $CaF_2$.

27. A system as in claim 1, wherein the input and output lenses each comprise a converging element selected from the group consisting of:

a positive miniscus;

an asymetic convex;

and/or a diverging element selected from the group consisting of:

a negative miniscus;

an asymetric concave.

28. A system as in claim 1 which is an ellipsometer or polarimeter system in which the input and output lenses are part of a system sequentially comprising:

a) a source of a spectroscopic beam electromagnetic radiation;

b) a polarizer element;

in either order elements c) and d):

c) optionally a compensator element;

d) said input lens;

e) a material system;

in either order elements f) and g):

f) said output lens;

g) optionally a compensator element;

h) an analyzer element; and i) a detector System.

29. A system as in claim 28 which further comprises beam directing means and/or windows located at least one selection from the group consisting of:

a) between said source of a spectroscopic beam electromagnetic radiation and said material system; and b) between said material system and said detector system.

30. A system for monitoring change in:

the intensity of; and/or the ratio of and/or the phase between orthogonal components in;

a beam of electromagnetic radiation which is caused by interaction with a material system;

said system comprising input and output lenses which are each of multiple element construction, wherein, for each of said input and output lenses at least two elements thereof are made from different materials, such that in use the focal length for each wavelength in a range of wavelengths is within an acceptable range of focal lengths, wherein said input and output lenses are characterized by a selection from the group consisting of:

both demonstrate birefringence; and one thereof demonstrates birefringence and the other not.

* * * * *